United States Patent
Blin et al.

(10) Patent No.: US 9,017,704 B2
(45) Date of Patent: *Apr. 28, 2015

(54) COMPOSITION COMPRISING A BLOCK POLYMER AND A FILM-FORMING AGENT

(75) Inventors: Xavier Blin, Paris (FR); Valerie De La Poterie, Lailly-en-Val (FR); Veronique Ferrari, Maison-Alfort (FR)

(73) Assignee: L'Oreal, Paris (FR)

( * ) Notice: Subject to any disclaimer, the term of this patent is extended or adjusted under 35 U.S.C. 154(b) by 2010 days.

This patent is subject to a terminal disclaimer.

(21) Appl. No.: 10/529,265

(22) PCT Filed: Sep. 26, 2003

(86) PCT No.: PCT/FR03/02849
§ 371 (c)(1),
(2), (4) Date: Sep. 28, 2005

(87) PCT Pub. No.: WO2004/028487
PCT Pub. Date: Apr. 8, 2004

(65) Prior Publication Data
US 2006/0093568 A1 May 4, 2006

(30) Foreign Application Priority Data

Sep. 26, 2002 (FR) .................... 02 11949
Dec. 20, 2002 (FR) .................... 02 16437
May 21, 2003 (FR) .................... 03 06121

(51) Int. Cl.
| | | |
|---|---|---|
| *A61K 8/72* | (2006.01) | |
| *A61K 31/74* | (2006.01) | |
| *A61K 47/06* | (2006.01) | |
| *A61Q 1/00* | (2006.01) | |
| *A61Q 19/00* | (2006.01) | |
| *C08L 51/00* | (2006.01) | |
| *A61K 8/26* | (2006.01) | |
| *A61K 8/81* | (2006.01) | |
| *A61K 8/891* | (2006.01) | |
| *A61K 8/90* | (2006.01) | |
| *A61K 8/92* | (2006.01) | |
| *A61Q 1/04* | (2006.01) | |
| *A61Q 1/06* | (2006.01) | |
| *A61Q 1/10* | (2006.01) | |
| *A61Q 3/02* | (2006.01) | |
| *C08F 265/04* | (2006.01) | |
| *C08F 265/06* | (2006.01) | |
| *C08F 291/00* | (2006.01) | |
| *C08F 293/00* | (2006.01) | |
| *C08L 53/00* | (2006.01) | |

(52) U.S. Cl.
CPC ............ *C08L 51/003* (2013.01); *A61K 8/26* (2013.01); *A61K 8/8111* (2013.01); *A61K 8/8152* (2013.01); *A61K 8/8182* (2013.01); *A61K 8/891* (2013.01); *A61K 8/90* (2013.01); *A61K 8/922* (2013.01); *A61K 8/927* (2013.01); *A61Q 1/04* (2013.01); *A61Q 1/06* (2013.01); *A61Q 1/10* (2013.01); *A61Q 3/02* (2013.01); *C08F 265/04* (2013.01); *C08F 265/06* (2013.01); *C08F 291/00* (2013.01); *C08F 293/005* (2013.01); *C08L 53/00* (2013.01); *A61K 2800/594* (2013.01); *Y10S 514/844* (2013.01); *Y10S 514/845* (2013.01); *Y10S 514/937* (2013.01)

(58) Field of Classification Search
CPC ....... A61K 8/022; A61K 8/0229; A61K 8/04; A61K 8/06; A61K 8/8111; A61K 8/123; A61K 8/129; A61K 8/135; A61K 8/141; A61Q 1/00; A61Q 1/02; A61Q 3/00; A61Q 5/00; A61Q 19/00
See application file for complete search history.

(56) References Cited

U.S. PATENT DOCUMENTS

| | | | |
|---|---|---|---|
| 811,910 A * | 2/1906 | Blin et al. ............... | 102/286 |
| 2,047,398 A | 7/1936 | Voss et al. | |
| 2,528,378 A | 10/1950 | Mannheimer et al. | |
| 2,723,248 A | 11/1955 | Wright | |
| 2,781,354 A | 2/1957 | Mannheimer et al. | |
| 3,673,160 A | 6/1972 | Buisson et al. | |
| 3,716,633 A | 2/1973 | Viout et al. | |
| 3,802,841 A | 4/1974 | Robin | |
| 3,836,537 A | 9/1974 | Boerwinkle et al. | |
| 3,910,862 A | 10/1975 | Barabas et al. | |

(Continued)

FOREIGN PATENT DOCUMENTS

| | | |
|---|---|---|
| DE | 2 330 956 | 1/1974 |
| DE | 100 22 247 | 11/2001 |

(Continued)

OTHER PUBLICATIONS

"Encyclopedia of Chemical Technology"; Kirk-Othmer; vol. 22, pp. 333-432, 3$^{rd}$ Edition, 1979, Wiley.

(Continued)

*Primary Examiner* — Lakshmi Channavajjala
(74) *Attorney, Agent, or Firm* — Oblon, Spivak, McClelland, Maier & Neustadt, L.L.P.

(57) ABSTRACT

The present invention provides a cosmetic composition comprising, in a cosmetically acceptable organic liquid medium, at least one film-forming ethylenic linear block polymer, and another film former.
The film former may be soluble or dispersible in the said organic liquid medium.
The composition may include an aqueous phase, in which case the film former may be soluble or dispersible in the aqueous phase.
The invention further provides for the use of the combination of such a block polymer and a film former for enhancing the staying power of the said composition on the keratin materials.

68 Claims, No Drawings

(56) References Cited

U.S. PATENT DOCUMENTS

| | | | |
|---|---|---|---|
| 3,915,921 A | 10/1975 | Schlatzer, Jr. |
| 3,925,542 A | 12/1975 | Viout et al. |
| 3,937,811 A | 2/1976 | Papantoniou et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,030,512 A | 6/1977 | Papantoniou et al. |
| 4,031,307 A | 6/1977 | DeMartino et al. |
| 4,032,628 A | 6/1977 | Papantoniou et al. |
| 4,070,533 A | 1/1978 | Papantoniou et al. |
| 4,076,912 A | 2/1978 | Papantoniou et al. |
| RE29,871 E | 12/1978 | Papantoniou et al. |
| 4,128,631 A | 12/1978 | Lundmark et al. |
| 4,129,711 A | 12/1978 | Viout et al. |
| 4,131,576 A | 12/1978 | Iovine |
| 4,137,208 A | 1/1979 | Elliott |
| 4,165,367 A | 8/1979 | Chakrabarti |
| 4,223,009 A | 9/1980 | Chakrabarti |
| 4,282,203 A | 8/1981 | Jacquet et al. |
| 4,289,752 A | 9/1981 | Mahieu et al. |
| 4,425,326 A | 1/1984 | Guillon et al. |
| 4,509,949 A | 4/1985 | Huang et al. |
| 4,693,935 A | 9/1987 | Mazurek |
| 4,728,571 A | 3/1988 | Clemens et al. |
| 4,887,622 A | 12/1989 | Gueret |
| 4,972,037 A | 11/1990 | Garbe et al. |
| 4,981,902 A | 1/1991 | Mitra et al. |
| 4,981,903 A | 1/1991 | Garbe et al. |
| 5,061,481 A | 10/1991 | Suzuki et al. |
| 5,110,582 A | 5/1992 | Hungerbuhler et al. |
| 5,156,911 A | 10/1992 | Stewart |
| 5,209,924 A | 5/1993 | Garbe et al. |
| 5,219,560 A | 6/1993 | Suzuki et al. |
| 5,362,485 A | 11/1994 | Hayama et al. |
| 5,391,631 A | 2/1995 | Porsch et al. |
| 5,468,477 A | 11/1995 | Kumar et al. |
| 5,472,798 A | 12/1995 | Kumazawa et al. |
| 5,492,426 A | 2/1996 | Gueret |
| 5,519,063 A | 5/1996 | Mondet et al. |
| 5,538,717 A | 7/1996 | La Poterie |
| 5,681,877 A | 10/1997 | Hosotte-Filbert et al. |
| 5,686,067 A | 11/1997 | Shih et al. |
| 5,690,918 A | 11/1997 | Jacks et al. |
| 5,711,940 A | 1/1998 | Kuentz et al. |
| 5,725,882 A | 3/1998 | Kumar et al. |
| 5,736,125 A | 4/1998 | Morawsky et al. |
| 5,747,013 A | 5/1998 | Mougin et al. |
| 5,756,635 A | 5/1998 | Michaud et al. |
| 5,772,347 A | 6/1998 | Gueret |
| 5,807,540 A | 9/1998 | Junino et al. |
| 5,849,275 A | 12/1998 | Calello et al. |
| 5,849,318 A | 12/1998 | Imai et al. |
| 5,879,095 A | 3/1999 | Gueret |
| 5,897,870 A | 4/1999 | Schehlmann et al. |
| 5,948,393 A | 9/1999 | Tomomasa et al. |
| 5,994,446 A | 11/1999 | Graulus et al. |
| 6,001,367 A | 12/1999 | Bazin et al. |
| 6,027,739 A | 2/2000 | Nichols |
| 6,033,650 A | 3/2000 | Calello et al. |
| 6,059,473 A | 5/2000 | Gueret |
| 6,074,654 A | 6/2000 | Drechsler et al. |
| 6,083,516 A | 7/2000 | Curtis et al. |
| 6,106,813 A | 8/2000 | Mondet et al. |
| 6,106,820 A | 8/2000 | Morrissey et al. |
| 6,120,781 A | 9/2000 | Le Bras et al. |
| 6,126,929 A | 10/2000 | Mougin |
| 6,132,742 A | 10/2000 | Le Bras et al. |
| 6,139,849 A | 10/2000 | Lesaulnier et al. |
| 6,140,431 A | 10/2000 | Kinker et al. |
| 6,153,206 A | 11/2000 | Anton et al. |
| 6,156,804 A | 12/2000 | Chevalier et al. |
| 6,160,054 A | 12/2000 | Schwindeman et al. |
| 6,165,457 A | 12/2000 | Midha et al. |
| 6,166,093 A | 12/2000 | Mougin et al. |
| 6,174,968 B1 | 1/2001 | Hoxmeier |
| 6,180,123 B1 | 1/2001 | Mondet |
| 6,197,883 B1 | 3/2001 | Schimmel et al. |
| 6,225,390 B1 | 5/2001 | Hoxmeier |
| 6,228,946 B1 | 5/2001 | Kitayama et al. |
| 6,228,967 B1 | 5/2001 | Fost et al. |
| 6,238,679 B1 | 5/2001 | De La Poterie et al. |
| 6,258,916 B1 | 7/2001 | Michaud et al. |
| 6,267,951 B1 | 7/2001 | Shah et al. |
| 6,268,466 B1 | 7/2001 | MacQueen et al. |
| 6,280,713 B1 | 8/2001 | Tranchant et al. |
| 6,303,105 B1 | 10/2001 | Shah et al. |
| 6,319,959 B1 | 11/2001 | Mougin et al. |
| 6,326,011 B1 | 12/2001 | Miyazawa et al. |
| 6,328,495 B1 | 12/2001 | Gueret |
| 6,342,237 B1 | 1/2002 | Bara |
| 6,372,876 B1 | 4/2002 | Kim et al. |
| 6,386,781 B1 | 5/2002 | Gueret |
| 6,395,265 B1 | 5/2002 | Mougin et al. |
| 6,399,691 B1 | 6/2002 | Melchiors et al. |
| 6,410,666 B1 | 6/2002 | Grubbs et al. |
| 6,412,496 B1 | 7/2002 | Gueret |
| 6,423,306 B2 | 7/2002 | Caes et al. |
| 6,464,969 B2 | 10/2002 | De La Poterie et al. |
| 6,484,731 B1 | 11/2002 | Lacout |
| 6,491,927 B1 | 12/2002 | Arnaud et al. |
| 6,518,364 B2 | 2/2003 | Charmot et al. |
| 6,531,535 B2 | 3/2003 | Melchiors et al. |
| 6,552,146 B1 | 4/2003 | Mougin |
| 6,581,610 B1 | 6/2003 | Gueret |
| 6,649,173 B1 | 11/2003 | Arnaud et al. |
| 6,663,855 B2 | 12/2003 | Frechet et al. |
| 6,663,885 B1 | 12/2003 | Hager et al. |
| 6,685,925 B2 | 2/2004 | Frechet et al. |
| 6,692,173 B2 | 2/2004 | Gueret |
| 6,692,733 B1 | 2/2004 | Mougin |
| 6,770,271 B2 | 8/2004 | Mondet et al. |
| 6,805,872 B2 | 10/2004 | Mougin |
| 6,833,419 B2 | 12/2004 | Morschhauser et al. |
| 6,843,611 B2 | 1/2005 | Blondeel et al. |
| 6,866,046 B2 | 3/2005 | Gueret |
| 6,881,780 B2 | 4/2005 | Bryant et al. |
| 6,890,522 B2 | 5/2005 | Frechet et al. |
| 6,891,011 B2 | 5/2005 | Morschhauser et al. |
| 6,905,696 B2 | 6/2005 | Marotta et al. |
| 6,946,518 B2 | 9/2005 | De La Poterie |
| 6,960,339 B1 | 11/2005 | Ferrari |
| 6,964,995 B2 | 11/2005 | Morschhauser et al. |
| 7,022,791 B2 | 4/2006 | Loffler et al. |
| 7,025,973 B2 | 4/2006 | Loffler et al. |
| 7,053,146 B2 | 5/2006 | Morschhauser et al. |
| 7,081,507 B2 | 7/2006 | Morschhauser et al. |
| 7,144,171 B2 | 12/2006 | Blondeel et al. |
| 7,151,137 B2 | 12/2006 | Morschhauser et al. |
| 7,176,170 B2 | 2/2007 | Dubief et al. |
| 7,186,405 B2 | 3/2007 | Loffler et al. |
| 7,186,774 B2 | 3/2007 | Morschhauser et al. |
| 7,244,421 B2 | 7/2007 | Loffler et al. |
| 7,279,154 B2 | 10/2007 | Loffler et al. |
| 7,297,328 B2 | 11/2007 | Loffler et al. |
| 7,332,155 B2 | 2/2008 | Loffler et al. |
| 7,358,303 B2 | 4/2008 | De La Poterie |
| 7,393,520 B2 | 7/2008 | Loffler et al. |
| 7,399,478 B2 | 7/2008 | Loffler et al. |
| 7,875,265 B2 * | 1/2011 | Blin et al. ............ 424/64 |
| 7,915,347 B2 * | 3/2011 | Lion et al. ............ 525/242 |
| 7,932,324 B2 * | 4/2011 | Lion et al. ............ 525/299 |
| 8,119,110 B2 | 2/2012 | Blin et al. |
| 2002/0015611 A1 | 2/2002 | Blondeel et al. |
| 2002/0018759 A1 | 2/2002 | Pagano et al. |
| 2002/0020424 A1 | 2/2002 | Gueret |
| 2002/0035237 A1 | 3/2002 | Lawson et al. |
| 2002/0054783 A1 | 5/2002 | Gueret |
| 2002/0055562 A1 | 5/2002 | Butuc |
| 2002/0061319 A1 | 5/2002 | Bernard et al. |
| 2002/0064539 A1 | 5/2002 | Philippe et al. |
| 2002/0076390 A1 | 6/2002 | Kantner et al. |
| 2002/0076425 A1 | 6/2002 | Mondet et al. |
| 2002/0098217 A1 | 7/2002 | Piot et al. |

(56) References Cited

U.S. PATENT DOCUMENTS

| | | |
|---|---|---|
| 2002/0115780 A1 | 8/2002 | Mougin |
| 2002/0150546 A1 | 10/2002 | Mougin et al. |
| 2002/0151638 A1 | 10/2002 | Melchiors et al. |
| 2002/0159965 A1 | 10/2002 | Frechet et al. |
| 2002/0160026 A1 | 10/2002 | Frechet et al. |
| 2003/0003154 A1 | 1/2003 | De La Poterie |
| 2003/0017124 A1 | 1/2003 | Agostini et al. |
| 2003/0017182 A1 | 1/2003 | Tournilhac |
| 2003/0021815 A9 | 1/2003 | Mondet et al. |
| 2003/0024074 A1 | 2/2003 | Hartman |
| 2003/0039621 A1 | 2/2003 | Arnaud et al. |
| 2003/0059392 A1 | 3/2003 | L'Alloret |
| 2003/0113285 A1 | 6/2003 | Meffert et al. |
| 2003/0124074 A1 | 7/2003 | Mougin et al. |
| 2003/0124079 A1 | 7/2003 | Mougin et al. |
| 2003/0185774 A1 | 10/2003 | Dobbs et al. |
| 2003/0191271 A1 | 10/2003 | Mondet et al. |
| 2004/0009136 A1 | 1/2004 | Dubief et al. |
| 2004/0013625 A1 | 1/2004 | Kanji |
| 2004/0014872 A1 | 1/2004 | Raether |
| 2004/0039101 A1 | 2/2004 | Dubief et al. |
| 2004/0052745 A1 | 3/2004 | Bernard et al. |
| 2004/0052752 A1 | 3/2004 | Samain et al. |
| 2004/0077788 A1 | 4/2004 | Guerra et al. |
| 2004/0091444 A1 | 5/2004 | Loffler et al. |
| 2004/0093676 A1 | 5/2004 | Vidal et al. |
| 2004/0096409 A1 | 5/2004 | Loeffler et al. |
| 2004/0096411 A1 | 5/2004 | Frechet et al. |
| 2004/0097657 A1 | 5/2004 | Morschhauser et al. |
| 2004/0109835 A1 | 6/2004 | Loffler et al. |
| 2004/0109836 A1 | 6/2004 | Loffler et al. |
| 2004/0109838 A1 | 6/2004 | Morschhauser et al. |
| 2004/0115148 A1 | 6/2004 | Loffler et al. |
| 2004/0115149 A1 | 6/2004 | Loffler et al. |
| 2004/0115157 A1 | 6/2004 | Loffler et al. |
| 2004/0116628 A1 | 6/2004 | Morschhauser et al. |
| 2004/0116634 A1 | 6/2004 | Morschhauser et al. |
| 2004/0120906 A1 | 6/2004 | Toumi et al. |
| 2004/0120920 A1 | 6/2004 | Lion et al. |
| 2004/0137020 A1 | 7/2004 | De La Poterie et al. |
| 2004/0137021 A1 | 7/2004 | De La Poterie et al. |
| 2004/0141937 A1 | 7/2004 | Loffler et al. |
| 2004/0141943 A1 | 7/2004 | Mougin et al. |
| 2004/0142831 A1 | 7/2004 | Jager Lezer |
| 2004/0167304 A1 | 8/2004 | Morschhauser et al. |
| 2004/0223933 A1 | 11/2004 | Hiwatashi et al. |
| 2004/0241118 A1 | 12/2004 | Simon et al. |
| 2005/0002724 A1 | 1/2005 | Blondeel et al. |
| 2005/0020779 A1 | 1/2005 | Mougin et al. |
| 2005/0032998 A1 | 2/2005 | Morschhauser et al. |
| 2005/0089536 A1 | 4/2005 | Loffler et al. |
| 2005/0095213 A1 | 5/2005 | Blin et al. |
| 2005/0106197 A1 | 5/2005 | Blin et al. |
| 2005/0129641 A1 | 6/2005 | Arnaud et al. |
| 2005/0201958 A1 | 9/2005 | De La Poterie |
| 2005/0212163 A1* | 9/2005 | Bausinger et al. ............ 264/113 |
| 2005/0220731 A1* | 10/2005 | Ilekti et al. ...................... 424/61 |
| 2005/0220747 A1 | 10/2005 | Lion et al. |
| 2005/0232887 A1 | 10/2005 | Morschhauser et al. |
| 2005/0287103 A1 | 12/2005 | Filippi et al. |
| 2006/0093568 A1 | 5/2006 | Blin et al. |
| 2006/0099164 A1 | 5/2006 | De La Poterie et al. |
| 2006/0099231 A1 | 5/2006 | De La Poterie et al. |
| 2006/0115444 A1 | 6/2006 | Blin et al. |
| 2006/0127334 A1 | 6/2006 | Ferrari et al. |
| 2006/0134032 A1 | 6/2006 | Ilekti et al. |
| 2006/0134038 A1 | 6/2006 | De La Poterie et al. |
| 2006/0134044 A1 | 6/2006 | Blin et al. |
| 2006/0134051 A1 | 6/2006 | Blin et al. |
| 2006/0147402 A1 | 7/2006 | Blin et al. |
| 2006/0147403 A1* | 7/2006 | Ferrari et al. ............. 424/70.16 |
| 2007/0003506 A1 | 1/2007 | Mougin et al. |
| 2007/0003507 A1 | 1/2007 | Mougin et al. |
| 2007/0134181 A1 | 6/2007 | Shimizu et al. |
| 2007/0166259 A1 | 7/2007 | Vicic et al. |
| 2008/0014232 A1 | 1/2008 | Arnaud et al. |
| 2008/0025934 A1* | 1/2008 | Lebre et al. ...................... 424/64 |
| 2008/0031837 A1* | 2/2008 | Farcet et al. ..................... 424/61 |
| 2008/0050329 A1 | 2/2008 | De La Poterie |
| 2008/0069793 A1 | 3/2008 | Loffler et al. |
| 2008/0107617 A1 | 5/2008 | Loffler et al. |
| 2008/0159965 A1 | 7/2008 | Mougin et al. |
| 2008/0207773 A1 | 8/2008 | Loffler et al. |
| 2008/0219943 A1 | 9/2008 | De La Poterie |
| 2009/0130037 A1 | 5/2009 | Thevenet et al. |
| 2010/0310489 A1 | 12/2010 | Barba |
| 2011/0020263 A1 | 1/2011 | Ilekti et al. |
| 2011/0280817 A1 | 11/2011 | Ramadan et al. |
| 2012/0171137 A1 | 7/2012 | Bradsaw et al. |
| 2012/0171139 A1 | 7/2012 | Bradshaw et al. |

FOREIGN PATENT DOCUMENTS

| | | |
|---|---|---|
| DE | 100 29 697 | 12/2001 |
| EP | 1 279 398 | 9/1971 |
| EP | 0 080 976 | 6/1983 |
| EP | 0 295 886 | 12/1988 |
| EP | 0 320 218 | 6/1989 |
| EP | 0 173 109 | 10/1989 |
| EP | 0 388 582 | 9/1990 |
| EP | 0 412 704 | 2/1991 |
| EP | 0 412 707 | 2/1991 |
| EP | 0 549 494 | 6/1993 |
| EP | 0 582 152 | 2/1994 |
| EP | 0 216 479 | 8/1994 |
| EP | 0 619 111 | 10/1994 |
| EP | 0 637 600 | 2/1995 |
| EP | 0 648 485 | 4/1995 |
| EP | 0 656 021 | 6/1995 |
| EP | 0 667 146 | 8/1995 |
| EP | 0 550 745 | 9/1995 |
| EP | 0 686 858 | 12/1995 |
| EP | 0 750 031 | 12/1996 |
| EP | 0 751 162 | 1/1997 |
| EP | 0 751 170 | 1/1997 |
| EP | 0 815 836 | 1/1998 |
| EP | 0 847 752 | 6/1998 |
| EP | 0 861 859 | 9/1998 |
| EP | 0 951 897 | 10/1999 |
| EP | 1 018 311 | 7/2000 |
| EP | 1 024 184 | 8/2000 |
| EP | 1 043 345 | 10/2000 |
| EP | 1 066 817 | 1/2001 |
| EP | 1 068 856 | 1/2001 |
| EP | 1 082 953 | 3/2001 |
| EP | 1 159 950 | 12/2001 |
| EP | 1 192 930 | 4/2002 |
| EP | 1 201 221 | 5/2002 |
| EP | 1 356 799 | 10/2003 |
| EP | 1 366 741 | 12/2003 |
| EP | 1 366 744 | 12/2003 |
| EP | 1 366 746 | 12/2003 |
| EP | 1 411 069 A2 | 4/2004 |
| EP | 0 955 039 | 5/2004 |
| EP | 1 421 928 A2 | 5/2004 |
| EP | 1 440 680 A1 | 7/2004 |
| EP | 1 518 534 | 3/2005 |
| EP | 1 518 535 | 3/2005 |
| EP | 1 604 634 | 12/2005 |
| FR | 1 222 944 | 6/1960 |
| FR | 1 400 366 | 4/1965 |
| FR | 1 564 110 | 3/1969 |
| FR | 1 580 545 | 9/1969 |
| FR | 2 077 143 | 9/1971 |
| FR | 2 079 785 | 11/1971 |
| FR | 2 140 977 | 1/1973 |
| FR | 2 232 303 | 1/1975 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 2 710 552 | 4/1995 |

(56) References Cited

FOREIGN PATENT DOCUMENTS

| | | |
|---|---|---|
| FR | 2 710 646 | 4/1995 |
| FR | 2 722 380 | 1/1996 |
| FR | 2 727 609 | 6/1996 |
| FR | 2 743 297 | 7/1997 |
| FR | 2 761 959 | 10/1998 |
| FR | 2 775 566 | 9/1999 |
| FR | 2 775 593 | 9/1999 |
| FR | 2 791 042 | 9/2000 |
| FR | 2 791 987 | 10/2000 |
| FR | 2 791 988 A1 | 10/2000 |
| FR | 2 792 190 | 10/2000 |
| FR | 2 792 618 | 10/2000 |
| FR | 2 796 529 | 1/2001 |
| FR | 2 798 061 | 3/2001 |
| FR | 2 803 743 | 7/2001 |
| FR | 2 806 273 | 9/2001 |
| FR | 2 296 402 | 11/2001 |
| FR | 2 809 306 | 11/2001 |
| FR | 2 811 993 | 1/2002 |
| FR | 2 814 365 | 3/2002 |
| FR | 2 816 503 | 5/2002 |
| FR | 2 823 101 | 10/2002 |
| FR | 2 823 103 | 10/2002 |
| FR | 2 827 514 A1 | 1/2003 |
| FR | 2 831 430 | 5/2003 |
| FR | 2 832 719 | 5/2003 |
| FR | 2 832 720 | 5/2003 |
| FR | 2 834 458 | 7/2003 |
| FR | 2 840 205 A1 | 12/2003 |
| FR | 2 840 209 A1 | 12/2003 |
| FR | 2 842 417 | 1/2004 |
| FR | 2 844 709 | 3/2004 |
| FR | 2 860 143 A1 | 4/2005 |
| FR | 2 860 156 A1 | 4/2005 |
| FR | 2 880 268 | 7/2006 |
| GB | 0 839 805 | 6/1960 |
| GB | 0 922 457 | 4/1963 |
| GB | 1 021 400 | 3/1966 |
| GB | 1 169 862 | 11/1969 |
| GB | 1 324 745 | 7/1973 |
| GB | 1 331 819 | 9/1973 |
| GB | 1 407 659 | 9/1975 |
| GB | 1 572 626 | 7/1980 |
| JP | 5-221829 | 8/1993 |
| JP | 06-279323 | 10/1994 |
| JP | 07-196450 | 8/1995 |
| JP | 07-309721 | 11/1995 |
| JP | 07-324017 | 12/1995 |
| JP | 08-119836 | 5/1996 |
| JP | 09-263518 | 10/1997 |
| JP | 10-506404 | 6/1998 |
| JP | H11-100307 | 4/1999 |
| JP | 11-124312 | 5/1999 |
| JP | 2000-83728 | 3/2000 |
| JP | 2000-319325 | 11/2000 |
| JP | 2000-319326 | 11/2000 |
| JP | 2001-348553 | 12/2001 |
| JP | 2001-527559 | 12/2001 |
| JP | 2002-201110 | 7/2002 |
| JP | 2002-201244 | 7/2002 |
| JP | 2003-40336 | 2/2003 |
| JP | 2003-73222 | 3/2003 |
| JP | 2003-081742 | 3/2003 |
| JP | 2003-286142 | 10/2003 |
| JP | 2004-2432 | 1/2004 |
| JP | 2004-2435 | 1/2004 |
| JP | 2004-149772 | 5/2004 |
| JP | 2004-269497 | 9/2004 |
| JP | 2005/104979 | 4/2005 |
| JP | 2006-503921 | 2/2006 |
| JP | 2006-507355 | 3/2006 |
| JP | 2006-507365 | 3/2006 |
| JP | 2006-507366 | 3/2006 |
| JP | 2006-507367 | 3/2006 |
| JP | 2006-151867 | 6/2006 |
| LU | 75370 | 7/1976 |
| LU | 75371 | 7/1976 |
| WO | WO 93/01797 | 2/1993 |
| WO | WO 93/23009 | 11/1993 |
| WO | WO 93/23446 | 11/1993 |
| WO | WO 94/03510 | 2/1994 |
| WO | WO 95/00578 | 1/1995 |
| WO | WO 95/03776 | 2/1995 |
| WO | WO 95/06078 | 3/1995 |
| WO | WO 96/10044 | 4/1996 |
| WO | WO 97/17057 | 5/1997 |
| WO | WO 98/31329 | 7/1998 |
| WO | WO 98/38981 | 9/1998 |
| WO | WO 98/42298 | 10/1998 |
| WO | WO 98/44012 | 10/1998 |
| WO | WO 98/51276 A1 | 11/1998 |
| WO | WO 00/26285 | 5/2000 |
| WO | WO 00/28948 | 5/2000 |
| WO | WO 00/40216 | 7/2000 |
| WO | WO 00/49997 | 8/2000 |
| WO | WO 01/03538 | 1/2001 |
| WO | WO 01/13863 | 3/2001 |
| WO | WO 01/19333 | 3/2001 |
| WO | WO 01/30886 | 5/2001 |
| WO | WO 01/43703 A1 | 6/2001 |
| WO | WO 01/51018 | 7/2001 |
| WO | WO 01/89470 A1 | 11/2001 |
| WO | WO 01/95871 | 12/2001 |
| WO | WO 02/05762 | 1/2002 |
| WO | WO 02/05765 | 1/2002 |
| WO | WO 02/28358 A1 | 4/2002 |
| WO | WO 02/34218 | 5/2002 |
| WO | WO 02/067877 | 9/2002 |
| WO | WO 02/080869 | 10/2002 |
| WO | WO 03/018423 | 3/2003 |
| WO | WO 03/046032 | 6/2003 |
| WO | WO 03/046033 | 6/2003 |
| WO | WO 2004/022009 | 3/2004 |
| WO | WO 2004/022010 | 3/2004 |
| WO | WO 2004/024700 A1 | 3/2004 |
| WO | WO 2004/028485 A2 | 4/2004 |
| WO | WO 2004/028487 A2 | 4/2004 |
| WO | WO 2004/028489 | 4/2004 |
| WO | WO 2004/028491 A2 | 4/2004 |
| WO | WO 2005/030158 A1 | 4/2005 |

OTHER PUBLICATIONS

English Language Derwent Abstract for EP 0 080 976.
English Language Derwent Abstract for EP 0 815 836.
English Language Derwent Abstract for FR 2 775 566.
English Language Derwent Abstract for FR 2 798 061.
English Language Derwent Abstract for FR 2 831 430.
English Language Derwent Abstract for WO 01/03538.
International Search Report for PCT Application No. PCT/FR03/02849.
Derwent Abstract of FR 2 860 156.
Derwent Abstract of JP 2001/348553.
Derwent Abstract of JP H11-100307.
Derwent Abstract of JP 2004/002435.
Derwent Abstract of JP 2004/002432.
Aldrich: Polymer Properties; 4th Ed. Catalog No. Z41, 247-3 (1999) published by John Wiley, New York.
Boutevin, B. et al., "Study of Morphological and Mechanical Properties of PP/PBT," Polymer Bulletin, 34, pp. 117-123, (1995).
Buzin, A. et al., "Calorimetric Study of Block-Copolymers of Poly(n-butyl Acrylate) and Gradient Poly(n-butyl acrylate-co-methyl methacrylate)" vol. 43, 2002, pp. 5563-5569.
Co-pending U.S. Appl. No. 10/528,698, filed Mar. 22, 2005; Inventors: Veronique Ferrari et al.
Co-pending U.S. Appl. No. 10/528,699, filed Mar. 22, 2005; Inventors: Philippe Ilekti et al.
Co-pending U.S. Appl. No. 10/528,835, filed Mar. 23, 2005; Inventors: Xavier Blin et al.
Co-pending U.S. Appl. No. 10/529,218, filed Mar. 25, 2005; Inventors: Xavier Blin et al.

(56) References Cited

OTHER PUBLICATIONS

Co-pending U.S. Appl. No. 10/529,264, filed Mar. 25, 2005; Inventors: Veronique Ferrari et al.
Co-pending U.S. Appl. No. 10/529,266, filed Mar. 25, 2005; Inventors: Xavier Blin et al.
Co-pending U.S. Appl. No. 10/529,267, filed Sep. 29, 2005; Inventors: Valerie De La Poterie et al.
Co-pending U.S. Appl. No. 10/529,318, filed Mar. 25, 2005; Inventors: Xavier Blin et al.
Co-pending U.S. Appl. No. 10/573,579, filed Dec. 26, 2006; Inventor: Marco Vicic et al.
Co-pending U.S. Appl. No. 10/585,817, filed Jan. 10, 2007; Inventor: Valerie De La Poterie.
Co-pending U.S. Appl. No. 10/585,818, filed Jul. 12, 2006; Inventors: Valerie De La Poterie.
Co-pending U.S. Appl. No. 10/670,388, filed Sep. 26, 2003; Inventors: Beatrice Toumi et al.
Co-pending U.S. Appl. No. 10/670,478, filed Sep. 26, 2003; Inventors: Bertrand Lion et al.
Co-pending U.S. Appl. No. 10/949,448, filed Sep. 27, 2004; Inventors: Xavier Blin et al.
Co-pending U.S. Appl. No. 11/086,906, filed Mar. 23, 2005; Inventors: Philippe Ilekti et al.
Co-pending U.S. Appl. No. 11/089,210, filed Mar. 25, 2005.
Co-pending U.S. Appl. No. 11/858,994, filed Sep. 21, 2007; Inventors: Bertrand Lion et al.
Co-pending U.S. Appl. No. 11/859,004, filed Sep. 21, 2007; Inventors: Bertrand Lion et al.
Co-pending U.S. Appl. No. 11/859,015, filed Sep. 21, 2007; Inventors: Bertrand Lion et al.
English Derwent Abstract for EP 1 082 953, dated Mar. 14, 2001.
English Derwent Abstract for EP 1 159 950, dated Dec. 5, 2001.
English Derwent Abstract for FR 2 803 743, dated Jul. 20, 2001.
English Derwent Abstract for FR 2 832 719, dated May 30, 2003.
English Derwent Abstract for WO 04/028489, dated Apr. 8, 2004.
English language Abstract of FR 2 710 552, dated Apr. 7, 1995.
English language Abstract of FR 2 710 646, dated Apr. 7, 1995.
English language Abstract of FR 2 791 987, dated Oct. 13, 2000.
English language Abstract of FR 2 832 720, dated May 30, 2003.
English language Abstract of FR 2 834 458, dated Jul. 11, 2003.
English language Abstract of JP 07-309721, dated Nov. 28, 1995.
English language Abstract of JP 08-119836, dated May 14, 1996.
English language Abstract of WO 01/13863, dated Mar. 1, 2001.
English language Abstract of WO 01/51018, dated Jul. 19, 2001.
English language Derwent Abstract for FR 2 792 190, dated Oct. 20, 2000.
English language Derwent Abstract for JP 06-279323, dated Oct. 4, 1994.
English language Derwent Abstract for JP 07-196450, dated Aug. 1, 1995.
English language Derwent Abstract for JP 09-263518, dated Oct. 7, 1997.
English language Derwent Abstract for JP 11-124312, dated May 11, 1999.
English language Derwent Abstract of DE 100 29 697, dated Dec. 20, 2001.
English language Derwent Abstract of EP 0 648 485, dated Apr. 19, 1995.
English language Derwent Abstract of FR 2 140 977, dated Jan. 19, 1973.
English language Derwent Abstract of JP 2002-201244, dated Jul. 19, 2002.
English language Derwent Abstract of JP 5-221829, dated Aug. 31, 1993.
European Search Report for EP 03 292 383, dated May 17, 2004, in Co-pending U.S. Appl. No. 10/670,388.
Fonnum, et al., Colloid Polym. Sci., 1993, 271: 380-389.
French Search Report for FR 02/11949 for Copending U.S. Appl. No. 10/670,478, dated Jul. 7, 2003.
French Search Report for FR 03/11340 for Copending U.S. Appl. No. 10/949,448, dated May 9, 2005.
French Search Report for FR 04/03090, for Copending U.S. Appl. No. 11/089,210, dated Sep. 30, 2004.
French Search Report for FR 04/50572, for Copending U.S. Appl. No. 11/086,906, dated Nov. 9, 2004.
Hamley, I.W., "Crystallization in Block Copolymers," Advances in Polymer Science, vol. 148, pp. 113-137 (1999).
Hansen, C.M., "The Three Dimensional Solubility Parameter—Key to Paint Component Affinities: I. Solvents, Plasticizers, Polymers, and Resins", Journal of Paint Technology, vol. 39, No. 505, pp. 104-117 (1967).
International Search Report for PCT/FR03/002844 (Priority Application for U.S. Appl. No. 10/529,318), dated May 14, 2005.
International Search Report for PCT/FR03/002847 (Priority Application for U.S. Appl. No. 10/529,266), dated May 17, 2004.
International Search Report for PCT/FR03/02841, dated Jun. 1, 2004.
International Search Report for PCT/FR03/02842 (Priority Application for U.S. Appl. No. 10/529,218), dated May 17, 2004.
International Search Report for PCT/FR03/02843 (Priority Application for U.S. Appl. No. 10/528,698), dated May 17, 2004.
International Search Report for PCT/FR03/02845 (Priority Application for U.S. Appl. No. 10/529,264), dated May 17, 2004.
International Search Report for PCT/FR03/02846 (Priority Application for U.S. Appl. No. 10/528,699), dated May 17, 2004.
International Search Report for PCT/FR03/02848 (Priority Application for U.S. Appl. No. 10/528,835), dated May 17, 2004.
International Search Report for PCT/IB2005/000230, dated May 27, 2005, (the PCT counterpart to co-pending U.S. Appl. No. 10/585,817).
International Search Report for PCT/IB2005/000236, dated Aug. 3, 2005, (the PCT counterpart to co-pending U.S. Appl. No. 10/585,818).
Nojima. S., "Melting Behavior of Poly (E-caprolactone)-block-polybutadiene Copolymers", Macromolecules, 32, 3727-3734 (1999).
Office Action mailed Aug. 12, 2005, in co-pending U.S. Appl. No. 10/670,478.
Office Action mailed Dec. 10, 2008, in co-pending U.S. Appl. No. 10/528,698.
Office Action mailed Dec. 23, 2008, in co-pending U.S. Appl. No. 10/529,266.
Office Action mailed Jan. 7, 2008, in co-pending U.S. Appl. No. 10/670,388.
Office Action mailed Jun. 12, 2009 in co-pending U.S. Appl. No. 11/086,906.
Office Action mailed Jun. 24, 2009 in co-pending U.S. Appl. No. 10/528,698.
Office Action mailed Jun. 24, 2009 in co-pending U.S. Appl. No. 10/529,267.
Office Action mailed Jun. 29, 2009 in co-pending U.S. Appl. No. 10/529,266.
Office Action mailed Jun. 4, 2009 in co-pending U.S. Appl. No. 10/670,478.
Office Action mailed Jun. 8, 2009 in co-pending U.S. Appl. No. 11/089,210.
Office Action mailed Mar. 12, 2009, in co-pending U.S. Appl. No. 10/529,218.
Office Action mailed Mar. 18, 2009, in co-pending U.S. Appl. No. 10/528,699.
Office Action mailed Mar. 18, 2009, in co-pending U.S. Appl. No. 10/573,579.
Office Action mailed Mar. 26, 2008, in co-pending U.S. Appl. No. 10/670,478.
Office Action mailed Mar. 7, 2006, in co-pending U.S. Appl. No. 10/670,478.
Office Action mailed May 3, 2007, in co-pending U.S. Appl. No. 10/670,478.
Office Action mailed Nov. 15, 2006, in co-pending U.S. Appl. No. 10/670,478.
Office Action mailed Nov. 25, 2008, in co-pending U.S. Appl. No. 10/949,448.

(56) References Cited

OTHER PUBLICATIONS

Office Action mailed Nov. 25, 2008, in co-pending U.S. Appl. No. 10/670,388.
Office Action mailed Oct. 1, 2008, in co-pending U.S. Appl. No. 10/529,318.
Office Action mailed Oct. 21, 2008, in co-pending U.S. Appl. No. 10/670,478.
Office Action mailed Sep. 7, 2007, in co-pending U.S. Appl. No. 10/670,478.
Pigeon, R. et al., Chimie Macromoleculaire Appliquee, No. 600, 40/41 (1074), pp. 139-158.
Porter, "Chapter 7: Non Ionics," Handbook of Surfactants, 1991, pp. 116-178, Chapman and Hall, New York.
Prince, L.M. ed., Macroemulsions Theory and Practice, Academic Press (1977), pp. 21-32.
Rangarajan P., et al., "Morphology of Semi-Crystalline Block Copolymers of Ethylene-(ethylene-alt-propylene)," Macromolecules, 26, 4640-4645 (1993).
Richter, P. et al., "Polymer Aggregates with Crystalline Cores: The System Poly(ethylene)-poly(ethylene-propylene)," Macromolecules, 30, 1053-1068 (1997).
Thermal_Transisitons_of_Homopolymers.pdf. Thermal Transistions of Homopolymers: Glass Transistion & Melting Point Data. Accessed online Dec. 19, 2008 at: http://www.sigmaaldrich.com/etc/medialib/docs/Aldrich/General_Information/thermal_transitions_of_homopolymers.Par.0001.File.tmp/thermal_transitions_of_homopolymers.pdf.
Co-pending U.S. Appl. No. 10/949,435, filed Sep. 27, 2004; Inventors: Xavier Blin et al.
Co-pending U.S. Appl. No. 11/878,067, filed Jul. 20, 2007; Inventors: Caroline Lebre et al.
Co-pending U.S. Appl. No. 11/878,849, filed Jul. 27, 2007; Inventors: Celine Farcet et al.
Cortazar, M. et al., "Glass Transition Temperatures of Plasticized Polyarylate,", Polymer Bulletin 18, 149-154 (1987).
English language Abstract of FR 2 357 241, dated Feb. 3, 1978.
English language Abstract of FR 2 880 268, dated Jul. 7, 2006.
English language Abstract of JP 2003-40336, Feb. 13, 2003.
English language Abstract of JP 2006-151867, dated Jun. 15, 2006.
Erichsen, J. et al., "Molecular Weight Dependence of the Surface Glass Transition of Polystyrene Films Investigated by the Embedding of Gold Nanoclusters," MRS Publication, 2001.
Flick, "Cosmetic Additives: An Industrial Guide", Noyes Publications, Park Ridge, NJ, p. 266 (1991).
French Search Report for FR 04/03088, dated Nov. 2, 2004.
French Search Report for FR 06/53144, dated Feb. 13, 2007.
French Search Report for FR 06/53154, dated Apr. 2, 2007.
HCAPLUS abstract 1964: 70247, abstracting: Develop. Ind. Microbiol., vol. 2, pp. 47-53 (1961).
Nojiri, A. et al., "Molecular Weight Dependence of the Glass Transition Temperature in Poly(vinyl acetate)," Japan J. Appl. Phys. 10 (1971), p. 803.
Specific Gravity and Viscosity of Liquid Table; available at http://wvvw.csgnetwork.com/sgvisc.html. Sesame seed oil information originally published Mar. 28, 2002.
Toniu, P. et al., "Process for Preparation of Block Polymers, Products Obtained by Means of the Process and Cosmetic Compositions Containing Them", 1973, French Patent Office, pp. 1-26 (English translation of French Patent No. FR2140977).
Office Action mailed Apr. 28, 2010, in co-pending U.S. Appl. No. 10/528,835.
Office Action mailed Aug. 12, 2009 in co-pending U.S. Appl. No. 10/949,448.
Office Action mailed Aug. 18, 2009 in co-pending U.S. Appl. No. 10/529,264.
Office Action mailed Dec. 3, 2009 in co-pending U.S. Appl. No. 10/528,698.
Office Action mailed Feb. 2, 2010, in co-pending U.S. Appl. No. 10/949,448.
Office Action mailed Feb. 27, 2009, in co-pending U.S. Appl. No. 11/878,849.
Office Action mailed Jan. 28, 2010, in co-pending U.S. Appl. No. 10/529,264.
Office Action mailed Jul. 21, 2009, in co-pending U.S. Appl. No. 11/878,067.
Office Action mailed Mar. 17, 2010, in co-pending U.S. Appl. No. 10/529,318.
Office Action mailed Mar. 18, 2009, in related U.S. Appl. No. 11/089,172.
Office Action mailed Mar. 30, 2010, in co-pending U.S. Appl. No. 11/089,210.
Office Action mailed Mar. 30, 2010, in co-pending U.S. Appl. No. 11/878,067.
Office Action mailed Nov. 17, 2009 in co-pending U.S. Appl. No. 10/528,835.
Office Action mailed Nov. 6, 2009 in co-pending U.S. Appl. No. 10/949,435.
Office Action mailed Oct. 27, 2009 in co-pending U.S. Appl. No. 10/529,218.
Office Action mailed Sep. 2, 2009 in co-pending U.S. Appl. No. 10/529,318.
Office Action mailed Sep. 28, 2009 in co-pending U.S. Appl. No. 10/670,478.
Office Action mailed Sep. 9, 2009, in co-pending U.S. Appl. No. 11/878,849.
Related U.S. Appl. No. 11/089,172, filed Mar. 25, 2005, Inventors: Katarina Benabdillah et al.
U.S. Appl. No. 13/729,631, filed Dec. 28, 2012, Kawaratani, et al.
Notice of Allowance in U.S. Appl. No. 10/670,478 dated Jul. 6, 2010.
Office Action mailed Aug. 2, 2010, in co-pending U.S. Appl. No. 10/949,435.
Office Action mailed Jul. 12, 2010, in co-pending U.S. Appl. No. 11/858,994.
Office Action mailed Jul. 28, 2010, in co-pending U.S. Appl. No. 10/529,264.
Office Action mailed Jul. 9, 2010, in co-pending U.S. Appl. No. 11/859,004.
Office Action mailed Jul. 9, 2010, in co-pending U.S. Appl. No. 11/859,015.
Office Action mailed May 12, 2010, in co-pending U.S. Appl. No. 11/086,906.
Office Action mailed May 28, 2010, in co-pending U.S. Appl. No. 10/573,579.
U.S. Appl. No. 14/354,719, filed Apr. 28, 2014, Bukawa, et al.
U.S. Appl. No. 14/359,791, filed May 21, 2014, Bui, et al.
U.S. Appl. No. 14/363,215, filed Jun. 5, 2014, Bukawa, et al.

* cited by examiner

COMPOSITION COMPRISING A BLOCK POLYMER AND A FILM-FORMING AGENT

The present invention relates to a cosmetic composition for making up or caring for human bodily and facial skin, the scalp included, the lips or epidermal derivatives of human beings, such as the hair, eyebrows, eyelashes or nails, which comprises a cosmetically acceptable medium comprising a film-forming block polymer in combination with another film former.

The composition may be a loose or compact powder, a foundation, a rouge, an eyeshadow, a concealer, a blusher, a lipstick, a lip balm, a lipgloss, a lip pencil, an eye pencil, a mascara, an eyeliner, a nail varnish or even a body makeup product or a skin colouring product.

Known compositions exhibit poor staying power over time, particularly as regards the colour. This poor staying power is characterized by an alteration in colour (colour change, fading), generally as a result of interaction with the sebum and/or perspiration secreted by the skin, in the case of foundation and of rouge or eyeshadow, or of interaction with the saliva, in the case of lipsticks. This alteration obliges the user to apply fresh makeup at frequent intervals, which may constitute a loss of time.

An improvement in staying power, particularly that of lipsticks, can be obtained by combining a volatile oil with a film-forming polymer, such as silicone resins. The resultant staying power properties, however, remain below consumer expectations.

There continues to be a need for a cosmetic product which leads to a deposit on keratin materials, in particular a makeup result, having good staying power.

The composition of the invention may in particular constitute a product for making up the body, the lips or the epidermal derivatives of human beings which has, in particular, non-therapeutic treatment and/or care properties. It constitutes in particular a lipstick or a lipgloss, a rouge or eyeshadow, a tattooing product, a mascara, an eyeliner, a nail varnish, an artificial skin-tanning product or a hair colouring or haircare product.

Surprisingly the inventors have found that, by combining a specific block polymer with a known film former, cosmetic compositions are obtained which lead to deposits, on keratin materials, whose staying power is superior to that of conventional compositions containing film formers.

More specifically the invention provides a cosmetic composition comprising an organic liquid medium, at least one film-forming ethylenic linear block polymer and at least one other film former.

In particular the invention provides a cosmetic composition comprising an organic liquid medium, at least one film-forming ethylenic linear block polymer and at least one other film former which is soluble in the organic liquid medium.

The invention also provides a cosmetic composition comprising an organic liquid medium, at least one film-forming ethylenic linear block polymer and at least one other, water-soluble film former.

The invention further provides a cosmetic composition comprising an organic liquid medium, at least one film-forming ethylenic linear block polymer and at least one aqueous dispersion of film-forming-polymer particles.

The invention further provides a cosmetic composition comprising an organic liquid medium, at least one film-forming ethylenic linear block polymer and at least one non-aqueous dispersion of film-forming polymer particles.

The film-forming ethylenic linear block polymer is advantageously non-elastomeric. The film-forming ethylenic linear block polymer is advantageously free from styrene units.

The invention also relates to a method of making up the skin and/or the lips and/or the epidermal derivatives which consists in applying to the skin and/or the lips and/or the epidermal derivatives the composition as defined above.

The composition according to the invention may be applied to the skin of the face, the scalp and the body, the mucosae such as the lips, the inside of the lower eyelids, and the epidermal derivatives such as the nails, eyebrows, hair, eyelashes, and even body hair.

Preferably the composition according to the invention is not a rinse-off composition.

The invention likewise relates to the cosmetic use of the composition defined above for enhancing the staying power of makeup on the skin and/or the lips and/or the epidermal derivatives.

In particular, in the case of an eyelash-coating composition or mascara, a composition of this kind makes it possible to obtain, following application to the eyelashes, a makeup film exhibiting good staying power, particularly with respect to water, during bathing or showering for example, to rubbing, particularly with the fingers, and/or to tears, perspiration or sebum.

The invention provides finally for the use of a film former in a composition comprising a block polymer as described above for the purpose of obtaining a composition which has good texture, is easy to apply and leads to a deposit with good staying power on the lips and/or the epidermal derivatives.

Block Polymer:

The composition according to the present invention comprises at least one block polymer. By "block" polymer is meant a polymer comprising at least 2 distinct blocks, preferably at least 3 distinct blocks.

According to one embodiment the block polymer of the composition according to the invention is an ethylenic polymer. By "ethylenic" polymer is meant a polymer obtained by polymerizing monomers comprising an ethylenic unsaturation.

According to one embodiment the block polymer of the composition according to the invention is a linear polymer. By opposition, a polymer having a non-linear structure is, for example, a polymer having a branched, starburst, graft or other structure.

According to one embodiment the block polymer of the composition according to the invention is a film-forming polymer. By "film-forming" polymer is meant a polymer capable of forming, by itself or in the presence of an auxiliary film-forming agent, a continuous and adherent film on a support, particularly on keratin materials.

According to one embodiment the block polymer of the composition according to the invention is a non-elastomeric polymer.

By "non-elastomeric polymer" is meant a polymer which, when subjected to a stress intended to stretch it (for example by 30% relative to its initial length), does not return to a length substantially identical to its initial length when the stress ceases.

More specifically the term "non-elastomeric polymer" denotes a polymer having an instantaneous recovery $R_i < 50\%$ and a retarded recovery $R_{2h} < 70\%$ after having undergone 30% elongation. Preferably $R_i$ is $<30\%$ and $R_{2h}$ is $<50\%$.

More specifically the non-elastomeric character of the polymer is determined in accordance with the following protocol:

A polymer film is prepared by pouring a solution of the polymer into a Teflon-coated mould and then drying it for 7 days in an environment controlled at 23±50° C. and 50±10% relative humidity.

This gives a film approximately 100 μm thick, from which rectangular specimens are cut (using a punch, for example) 15 mm wide and 80 mm long.

This sample is subjected to a tensile stress by means of an apparatus sold under the reference Zwick, under the same temperature and humidity conditions as for drying.

The specimens are stretched at a speed of 50 mm/min, and the distance between the jaws is 50 mm, corresponding to the initial length ($l_0$) of the specimen.

The instantaneous recovery Ri is determined as follows:
the specimen is stretched by 30% ($\epsilon_{max}$), i.e. about 0.3 times its initial length ($l_0$);
the stress is released by applying a return speed equal to the tensile speed, i.e. 50 mm/min, and the residual elongation of the specimen is measured as a percentage, after return to zero stress ($\epsilon_i$).

The instantaneous recovery in % ($R_i$) is given by the formula below:

$$R_i = (\epsilon_{max} - \epsilon_i)/\epsilon_{max} \times 100$$

To determine the retarded recovery the residual elongation of the specimen is measured as a percentage ($\epsilon_{2h}$) 2 hours after return to zero stress.

The retarded recovery in % ($R_{2h}$) is given by the formula below:

$$R_{2h} = (\epsilon_{max} - \epsilon_{2h})/\epsilon_{max} \times 100$$

Purely by way of indication, a polymer according to one embodiment of the invention possesses an instantaneous recovery $R_i$ of 10% and a retarded recovery $R_{2h}$ of 30%.

According to another embodiment the block polymer of the composition according to the invention does not include a styrene unit. By polymer free from styrene units is meant a polymer containing less than 10%, preferably less than 5%, preferably less than 2%, more preferably less than 1% by weight i) of styrene unit of formula —CH($C_6H_5$)—$CH_2$— or ii) of substituted styrene unit, for example methylstyrene, chlorostyrene or chloromethylstyrene.

According to one embodiment the block polymer of the composition according to the invention is obtained from aliphatic ethylenic monomers. By aliphatic monomer is meant a monomer containing no aromatic group.

According to one embodiment the block polymer is an ethylenic polymer obtained from aliphatic ethylenic monomers comprising a carbon-carbon double bond and at least one ester group —COO— or amide group —CON—. The ester group may be bonded to one of the two unsaturated carbons via the carbon atom or the oxygen atom. The amide group may be bonded to one of the two unsaturated carbons via the carbon atom or the nitrogen atom.

According to one mode of implementation the block polymer comprises at least one first block and at least one second block.

By "at least" one block is meant one or more blocks.

It is specified that, in the text above and below, the terms "first" and "second" blocks in no way condition the order of the said blocks (or sequences) in the structure of the polymer.

According to one mode of implementation the block polymer comprises at least one first block and at least one second block which have different glass transition temperatures (Tgs).

In this mode of implementation the first and second blocks may be connected to one another by an intermediate segment having a glass transition temperature between the glass transition temperatures of the first and second blocks.

According to one mode of implementation the block polymer comprises at least one first block and at least one second block connected to one another by an intermediate segment comprising at least one constituent monomer of the first block and at least one constituent monomer of the second block.

Preferably the intermediate block is obtained essentially from constituent monomers of the first block and of the second block.

By "essentially" is meant to an extent of at least 85%, preferably at least 90%, more preferably 95% and more preferably still 100%.

Advantageously the intermediate segment comprising at least one constituent monomer of the first block and at least one constituent monomer of the second block of the polymer is a random polymer.

According to one mode of implementation the block polymer comprises at least one first block and at least one second block which are incompatible in the organic liquid medium of the composition of the invention.

By "blocks incompatible with one another" is meant that the mixture formed from the polymer corresponding to the first block and from the polymer corresponding to the second block is not miscible in the organic liquid that is in a majority by weight in the organic liquid medium of the composition, at ambient temperature (25° C.) and atmospheric pressure ($10^5$ Pa), for a polymers mixture content greater than or equal to 5% by weight, relative to the total weight of the mixture (polymers and majority organic liquid), with the provisos that
i) the said polymers are present in the mixture in an amount such that the respective weight ratio ranges from 10/90 to 90/10, and that
ii) each of the polymers corresponding to the first and second blocks has an average molecular mass (by weight or by number) equal to that of the block polymer+/−15%.

In the case where the organic liquid medium comprises a mixture of organic liquids, should two or more liquids be present in identical mass proportions, the said polymers mixture is not miscible in at least one of them.

In the case where the organic liquid medium comprises a single organic liquid, the said liquid, quite obviously, constitutes the liquid that is in a majority by weight.

By "organic liquid medium" is meant a medium comprising at least one organic liquid, in other words at least one organic compound which is liquid at ambient temperature (25° C.) and atmospheric pressure ($10^5$ Pa). According to one mode of implementation the majority liquid of the organic liquid medium is a volatile or non-volatile oil (fat). Preferably the organic liquid is cosmetically acceptable (acceptable tolerance, toxicology and feel). The organic liquid medium is cosmetically acceptable in the sense that it is compatible with keratin materials, such as the oils or organic solvents commonly employed in cosmetic compositions.

According to one mode of implementation the majority liquid of the organic liquid medium is the polymerization solvent or one of the polymerization solvents of the block polymer, as are described below.

By polymerization solvent is meant a solvent or a mixture of solvents. The polymerization solvent may be selected in particular from ethyl acetate, butyl acetate, alcohols such as isopropanol and ethanol, aliphatic alkanes such as isododecane, and mixtures thereof. Preferably the polymerization solvent is a mixture of butyl acetate and isopropanol, or isododecane.

Generally speaking, the block polymer may be incorporated into the composition at a high solids content, typically more than 10%, more than 20% and more preferably more than 30% and more preferably still more than 45% by weight relative to the total weight of the composition, while being easy to formulate.

Preferentially the block polymer does not include silicon atoms in its skeleton. By "skeleton" is meant the main chain of the polymer, as opposed to the pendent side chains.

Preferably the polymer according to the invention is not water-soluble, which is to say that the polymer is not soluble in water or in a mixture of water and linear or branched lower monoalcohols having 2 to 5 carbon atoms, such as ethanol, isopropanol or n-propanol, without a change in pH, at an active substance content of at least 1% by weight, at ambient temperature (25° C.).

According to one mode of implementation the block polymer has a polydispersity index I of greater than 2.

Advantageously the block polymer used in the compositions according to the invention has a polydispersity index I of greater than 2, ranging for example from 2 to 9, preferably greater than or equal to 2.5, ranging for example from 2.5 to 8, and better still greater than or equal to 2.8, and in particular ranging from 2.8 to 6.

The polydispersity index I of the polymer is equal to the ratio of the weight-average mass Mw to the number-average mass Mn.

The weight-average (Mw) and number-average (Mn) molar masses are determined by liquid chromatography by gel permeation (THF solvent, calibration curve established with standards of linear polystyrene, refractometric detector).

The weight-average mass (Mw) of the block polymer is preferably less than or equal to 300 000, and ranges for example from 35 000 to 200 000, better still from 45 000 to 150 000.

The number-average mass (Mn) of the block polymer is preferably less than or equal to 70 000, and ranges for example from 10 000 to 60 000, better still from 12 000 to 50 000.

Each block or sequence of the block polymer is obtained from one type of monomer or from two or more different types of monomers.

This signifies that each block may be composed of a homopolymer or of a copolymer; this copolymer, constituting the block, may in turn be random or alternating.

The glass transition temperatures indicated for the first and second blocks may be theoretical Tgs determined from the theoretical Tgs of the constituent monomers of each of the blocks, which can be found in a reference manual such as the Polymer Handbook, 3rd ed., 1989, John Wiley, according to the following relationship, called Fox's Law:

$$\frac{1/Tg = \sum_i (\bar{\omega}_i / Tg_i)}{i},$$

$\bar{\omega}_i$ being the mass fraction of the monomer i in the block in question and $Tg_i$ being the glass transition temperature of the homopolymer of the monomer i.

Unless indicated otherwise, the Tgs indicated for the first and second blocks in the present specification are theoretical Tgs.

The difference between the glass transition temperatures of the first and second blocks is generally greater than 10° C., preferably greater than 20° C. and more preferably greater than 30° C.

In particular the block polymer comprises at least one first block and at least one second block such that the first block may be selected from:

a) a block with a Tg of greater than or equal to 40° C.,
b) a block with a Tg of less than or equal to 20° C.,
c) a block with a Tg of between 20 and 40° C., and the second block may be selected from a category a), b) or c) different from the first block.

In the present invention, the expression "between . . . and . . . " is intended to denote a range of values for which the limits mentioned are excluded, and the expression "from . . . to . . . " and "ranging from . . . to . . . " is intended to denote a range of values for which the limits are included.

a) Block with a Tg of Greater than or Equal to 40° C.

The block with a Tg of greater than or equal to 40° C. has, for example, a Tg ranging from 40 to 150° C., preferably greater than or equal to 50° C., ranging for example from 50° C. to 120° C., and better still greater than or equal to 60° C., ranging for example from 60° C. to 120° C.

The block with a Tg of greater than or equal to 40° C. may be a homopolymer or a copolymer.

The block with a Tg of greater than or equal to 40° C. may be obtained totally or partly from one or more monomers which are such that the homopolymer prepared from these monomers has a glass transition temperature of greater than or equal to 40° C.

In the case where this block is a homopolymer, it is obtained from monomers which are such that the homopolymers prepared from these monomers have glass transition temperatures of greater than or equal to 40° C. This first block may be a homopolymer composed of a single type of monomer (for which the Tg of the corresponding homopolymer is greater than or equal to 40° C.).

In the case where the first block is a copolymer, it may be obtained totally or partly from one or more monomers, the nature and concentration of which are selected such that the Tg of the resulting copolymer is greater than or equal to 40° C. The copolymer may comprise, for example:

monomers which are such that the homopolymers prepared from these monomers have Tgs of greater than or equal to 40° C., for example a Tg ranging from 40 to 150° C., preferably greater than or equal to 50° C., ranging for example from 50° C. to 120° C., and better still greater than or equal to 60° C., ranging for example from 60° C. to 120° C., and monomers which are such that the homopolymers prepared from these monomers have Tgs of less than 40° C., selected from monomers with a Tg of between 20 to 40° C. and/or monomers with a Tg of less than or equal to 20° C., for example a Tg ranging from −100 to 20° C., preferably less than 15° C., especially ranging from −80° C. to 15° C. and better still less than 10° C., for example ranging from −50° C. to 0° C., as described later.

The monomers whose homopolymers have a glass transition temperature of greater than or equal to 40° C. are selected, preferably, from the following monomers, also known as principal monomers:

methacrylates of formula $CH_2=C(CH_3)-COOR_1$ in which $R_1$ represents a linear or branched unsubstituted alkyl group containing from 1 to 4 carbon atoms, such as a methyl, ethyl, propyl or isobutyl group, or $R_1$ represents a $C_4$ to $C_{12}$ cycloalkyl group;

acrylates of formula $CH_2=CH-COOR_2$ in which $R_2$ represents a $C_4$ to $C_{12}$ cycloalkyl group, such as isobornyl acrylate or a tert-butyl group;

(meth)acrylamides of formula:

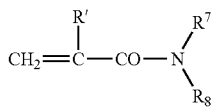

where $R_7$ and $R_8$, which are identical or different, each represent a hydrogen atom or a linear or branched $C_1$ to $C_{12}$ alkyl group, such as an n-butyl, t-butyl, isopropyl, isohexyl, isooctyl or isononyl group; or $R_7$ represents H and $R_8$ represents a 1,1-dimethyl-3-oxobutyl group and R' denotes H or methyl. Examples of monomers that may be mentioned include N-butylacrylamide, N-t-butylacrylamide, N-isopropylacrylamide, N,N-dimethylacrylamide and N,N-dibutylacrylamide;

and mixtures thereof.

Principal monomers that are particularly preferred are methyl methacrylate, isobutyl (meth)acrylate and isobornyl (meth)acrylate, and mixtures thereof.

b) Block with a Tg of Less Than or Equal to 20° C.

The block with a Tg of less than or equal to 20° C. has, for example, a Tg ranging from −100 to 20° C., preferably less than or equal to 15° C., especially ranging from −80° C. to 15° C. and better still less than or equal to 10° C., for example ranging from −50° C. to 0° C.

The block with a Tg of less than or equal to 20° C. may be a homopolymer or a copolymer.

The block with a Tg of less than or equal to 20° C. may be obtained totally or partly from one or more monomers which are such that the homopolymer prepared from these monomers has a glass transition temperature of less than or equal to 20° C.

In the case where this block is a homopolymer, it is obtained from monomers which are such that the homopolymers prepared from these monomers have glass transition temperatures of less than or equal to 20° C. This second block may be a homopolymer composed of a single type of monomer (for which the Tg of the corresponding homopolymer is less than or equal to 20° C.).

In the case where the block with a Tg of less than or equal to 20° C. is a copolymer, it may be obtained totally or partly from one or more monomers, the nature and concentration of which are selected such that the Tg of the resulting copolymer is less than or equal to 20° C.

It may comprise, for example
  one or more monomers whose corresponding homopolymer has a Tg of less than or equal to 20° C., for example a Tg ranging from −100° C. to 20° C., preferably less than 15° C., especially ranging from −80° C. to 15° C. and better still less than 10° C., for example ranging from −50° C. to 0° C., and
  one or more monomers whose corresponding homopolymer has a Tg of greater than 20° C., such as monomers with a Tg of greater than or equal to 40° C., for example a Tg ranging from 40 to 150° C., preferably greater than or equal to 50° C., ranging for example from 50° C. to 120° C. and better still greater than or equal to 60° C., ranging for example from 60° C. to 120° C. and/or monomers with a Tg of between 20 and 40° C., as described above.

Preferably the block with a Tg of less than or equal to 20° C. is a homopolymer.

The monomers whose homopolymer has a Tg of less than or equal to 20° C. are selected, preferably, from the following monomers, or principal monomer:

acrylates of formula $CH_2=CHCOOR_3$, $R_3$ representing a linear or branched $C_1$ to $C_{12}$ unsubstituted alkyl group, with the exception of the tert-butyl group, in which one or more heteroatoms selected from O, N and S is (are) optionally intercalated;

methacrylates of formula $CH_2=C(CH_3)-COOR_4$, $R_4$ representing a linear or branched $C_6$ to $C_{12}$ unsubstituted alkyl group, in which one or more hetero-atoms selected from O, N and S is (are) optionally intercalated;

vinyl esters of formula $R_5-CO-O-CH=CH_2$ where $R_5$ represents a linear or branched $C_4$ to $C_{12}$ alkyl group;

$C_4$ to $C_{12}$ alkyl vinyl ethers;

N—($C_4$ to $C_{12}$ alkyl) acrylamides, such as N-octylacrylamide;

and mixtures thereof.

The principal monomers that are particularly preferred for the block with a Tg of less than or equal to 20° C. are alkyl acrylates in which the alkyl chain contains from 1 to 10 carbon atoms, with the exception of the tert-butyl group, such as methyl acrylate, isobutyl acrylate and 2-ethylhexyl acrylate, and mixtures thereof.

c) Block with a Tg of Between 20 and 40° C.

The block with a Tg of between 20 and 40° C. may be a homopolymer or a copolymer.

The block with a Tg of between 20 and 40° C. may be obtained totally or partly from one or more monomers which are such that the homopolymer prepared from these monomers has a glass transition temperature of between 20 and 40° C.

The block with a Tg of between 20 and 40° C. may be obtained totally or partly from monomers which are such that the corresponding homopolymer has a Tg of greater than or equal to 40° C. and from monomers which are such that the corresponding homopolymer has a Tg of less than or equal to 20° C.

In the case where this block is a homopolymer, it is obtained from monomers (or principal monomers) which are such that the homopolymers prepared from these monomers have glass transition temperatures of between 20 and 40° C. This first block may be a homopolymer composed of a single type of monomer (for which the Tg of the corresponding homopolymer ranges from 20° C. to 40° C.).

The monomers whose homopolymer has a glass transition temperature of between 20 and 40° C. are selected, preferably, from n-butyl methacrylate, cyclodecyl acrylate, neopentyl acrylate and isodecylacrylamide, and mixtures thereof.

In the case where the block with a Tg of between 20 and 40° C. is a copolymer, it is obtained totally or partly from one or more monomers (or principal monomers) the nature and concentration of which are selected such that the Tg of the resulting copolymer is between 20 and 40° C.

Advantageously the block with a Tg of between 20 and 40° C. is a copolymer obtained totally or partly from:
  principal monomers whose corresponding homopolymer has a Tg of greater than or equal to 40° C., for example a Tg ranging from 40° C. to 150° C., preferably greater than or equal to 50° C., ranging for example from 50 to 120° C. and better still greater than or equal to 60° C., ranging for example from 60° C. to 120° C., as described above; and/or
  principal monomers whose corresponding homopolymer has a Tg of less than or equal to 20° C., for example a Tg ranging from −100 to 20° C., preferably less than or equal to 15° C., especially ranging from −80° C. to 15° C. and better still less than or equal to 10° C., for example ranging from −50° C. to 0° C., as described above, the said monomers being selected such that the Tg of the copolymer forming the first block is between 20 and 40° C.

Such principal monomers are selected, for example, from methyl methacrylate, isobornyl acrylate and methacrylate, butyl acrylate and 2-ethylhexyl acrylate, and mixtures thereof.

Preferably the proportion of the second block with a Tg of less than or equal to 20° C. ranges from 10% to 85%, better still from 20% to 70% and even better still from 20% to 50% by weight of the polymer.

Preferably each of the first and second blocks comprises at least one monomer selected from acrylic acid, the esters of acrylic acid, (meth)acrylic acid, the esters of (meth)acrylic acid, and mixtures thereof.

Advantageously each of the first and second blocks is obtained totally from at least one monomer selected from acrylic acid, the esters of acrylic acid, (meth)acrylic acid, the esters of (meth)acrylic acid, and mixtures thereof.

However, each of the blocks may contain in minority proportion at least one constituent monomer of the other block.

Thus the first block may contain at least one constituent monomer of the second block, and vice versa.

Each of the first and/or second blocks may comprise, in addition to the monomers indicated above, one or more other monomers known as additional monomers, which are different from the principal monomers mentioned above.

The nature and amount of this or these additional monomer(s) are selected such that the block in which they are present has the desired glass transition temperature.

This additional monomer is selected, for example, from:
a) hydrophilic monomers such as:
   ethylenically unsaturated monomers comprising at least one carboxylic or sulphonic acid function, for instance: acrylic acid, methacrylic acid, crotonic acid, maleic anhydride, itaconic acid, fumaric acid, maleic acid, acrylamidopropanesulphonic acid, vinylbenzoic acid, vinylphosphoric acid, and salts thereof;
   ethylenically unsaturated monomers comprising at least one tertiary amine function, for instance 2-vinylpyridine, 4-vinylpyridine, dimethylaminoethyl methacrylate, diethylaminoethyl methacrylate and dimethylaminopropylmethacrylamide, and salts thereof;
   methacrylates of formula $CH_2=C(CH_3)-COOR_6$ in which $R_6$ represents a linear or branched alkyl group containing from 1 to 4 carbon atoms, such as a methyl, ethyl, propyl or isobutyl group, the said alkyl group being substituted by one or more substituents selected from hydroxyl groups (for instance 2-hydroxypropyl methacrylate and 2-hydroxyethyl methacrylate) and halogen atoms (Cl, Br, I or F), such as trifluoroethyl methacrylate;
   methacrylates of formula $CH_2=C(CH_3)-COOR_9$, $R_9$ representing a linear or branched $C_6$ to $C_{12}$ alkyl group in which one or more heteroatoms selected from O, N and S is (are) optionally intercalated, the said alkyl group being substituted by one or more substituents selected from hydroxyl groups and halogen atoms (Cl, Br, I or F);
   acrylates of formula $CH_2=CHCOOR_{10}$, $R_{10}$ representing a linear or branched $C_1$ to $C_{12}$ alkyl group substituted by one or more substituents selected from hydroxyl groups and halogen atoms (Cl, Br, I or F), such as 2-hydroxypropyl acrylate and 2-hydroxyethyl acrylate, or $R_{10}$ represents a $C_1$ to $C_{12}$ alkyl-O-POE (polyoxyethylene) with repetition of the oxyethylene unit from 5 to 30 times, for example methoxy-POE, or $R_{10}$ represents a polyoxyethylenated group comprising from 5 to 30 ethylene oxide units;
b) ethylenically unsaturated monomers comprising one or more silicon atoms, such as methacryloxypropyltrimethoxysilane and methacryloxypropyltris(trimethylsiloxy)silane;
   and mixtures thereof.

Additional monomers that are particularly preferred are acrylic acid, methacrylic acid and trifluoroethyl methacrylate, and mixtures thereof.

According to one embodiment, each of the first and second blocks of the block polymer comprises at least one monomer selected from esters of (meth)acrylic acid and optionally at least one additional monomer such as (meth)acrylic acid, and mixtures thereof.

According to another embodiment, each of the first and second blocks of the block polymer is obtained totally from at least one monomer selected from esters of (meth)acrylic acid and optionally at least one additional monomer such as (meth)acrylic acid, and mixtures thereof.

According to one preferred embodiment, the block polymer is a non-silicone polymer, i.e. a polymer free of silicon atoms.

This or these additional monomer(s) generally represent(s) an amount of less than or equal to 30% by weight, for example from 1% to 30% by weight, preferably from 5% to 20% by weight and more preferably from 7% to 15% by weight, relative to the total weight of the first and/or second blocks.

The block polymer may be obtained by free-radical solution polymerization according to the following preparation process:
   a portion of the polymerization solvent is introduced into a suitable reactor and heated until the adequate temperature for the polymerization is reached (typically between 60 and 120° C.),
   once this temperature is reached, the constituent monomers of the first block are introduced in the presence of a portion of the polymerization initiator,
   after a time T corresponding to a maximum degree of conversion of 90%, the constituent monomers of the second block and the rest of the initiator are introduced,
   the mixture is left to react for a time T' (ranging from 3 to 6 hours), after which the mixture is cooled to ambient temperature,
   the polymer in solution in the polymerization solvent is obtained.

First Embodiment

According to a first embodiment, the block polymer comprises a first block with a Tg of greater than or equal to 40° C., as described above in a), and a second block with a Tg of less than or equal to 20° C., as described above in b).

Preferably the first block with a Tg of greater than or equal to 40° C. is a copolymer obtained from monomers which are such that the homopolymer prepared from these monomers has a glass transition temperature of greater than or equal to 40° C., such as the monomers described above.

Advantageously the second block with a Tg of less than or equal to 20° C. is a homopolymer obtained from monomers which are such that the homopolymer prepared from these monomers has a glass transition temperature of less than or equal to 20° C., such as the monomers described above.

Preferably the proportion of the block with a Tg of greater than or equal to 40° C. ranges from 20% to 90%, better still from 30% to 80% and even better still from 50% to 70% by weight of the polymer.

Preferably the proportion of the block with a Tg of less than or equal to 20° C. ranges from 5% to 75%, preferably from 15% to 50% and better still from 25% to 45% by weight of the polymer.

Thus, according to a first variant, the polymer according to the invention may comprise:
- a first block with a Tg of greater than or equal to 40° C., for example having a Tg ranging from 70 to 110° C., which is a methyl methacrylate/acrylic acid copolymer,
- a second block with a Tg of less than or equal to 20° C., for example ranging from 0 to 20° C., which is a methyl acrylate homopolymer, and
- an intermediate block which is a methyl methacrylate/acrylic acid/methyl acrylate copolymer.

According to a second variant, the polymer according to the invention may comprise:
- a first block with a Tg of greater than or equal to 40° C., for example ranging from 70 to 100° C., which is a methyl methacrylate/acrylic acid/trifluoroethyl methacrylate copolymer,
- a second block with a Tg of less than or equal to 20° C., for example ranging from 0 to 20° C., which is a methyl acrylate homopolymer, and
- an intermediate block which is a methyl methacrylate/acrylic acid/methyl acrylate/trifluoroethyl methacrylate random copolymer.

According to a third variant, the polymer according to the invention may comprise:
- a first block with a Tg of greater than or equal to 40° C., for example ranging from 85 to 115° C., which is an isobornyl acrylate/isobutyl methacrylate copolymer,
- a second block with a Tg of less than or equal to 20° C., for example ranging from −85 to −55° C., which is a 2-ethylhexyl acrylate homopolymer, and
- an intermediate block which is an isobornyl acrylate/isobutyl methacrylate/2-ethylhexyl acrylate random copolymer.

According to a fourth variant, the polymer according to the invention may comprise:
- a first block with a Tg of greater than or equal to 40° C., for example ranging from 85 to 115° C., which is an isobornyl acrylate/methyl methacrylate copolymer,
- a second block with a Tg of less than or equal to 20° C., for example ranging from −85 to −55° C., which is a 2-ethylhexyl acrylate homopolymer, and
- an intermediate block which is an isobornyl acrylate/methyl methacrylate/2-ethylhexyl acrylate random copolymer.

According to a fifth variant, the polymer according to the invention may comprise:
- a first block with a Tg of greater than or equal to 40° C., for example ranging from 95 to 125° C., which is an isobornyl acrylate/isobornyl methacrylate copolymer,
- a second block with a Tg of less than or equal to 20° C., for example ranging from −85 to −55° C., which is a 2-ethylhexyl acrylate homopolymer, and
- an intermediate block which is an isobornyl acrylate/isobornyl methacrylate/2-ethylhexyl acrylate random copolymer.

According to a sixth variant, the polymer according to the invention may comprise:
- a first block with a Tg of greater than or equal to 40° C., for example ranging from 85 to 115° C., which is an isobornyl methacrylate/isobutyl methacrylate copolymer,
- a second block with a Tg of less than or equal to 20° C., for example ranging from −35 to −5° C., which is an isobutyl acrylate homopolymer, and
- an intermediate block which is an isobornyl methacrylate/isobutyl methacrylate/isobutyl acrylate random copolymer.

According to a seventh variant, the polymer according to the invention may comprise:
- a first block with a Tg of greater than or equal to 40° C., for example ranging from 95 to 125° C., which is an isobornyl acrylate/isobornyl methacrylate copolymer,
- a second block with a Tg of less than or equal to 20° C., for example ranging from −35 to −5° C., which is an isobutyl acrylate homopolymer, and
- an intermediate block which is an isobornyl acrylate/isobornyl methacrylate/isobutyl acrylate random copolymer.

According to an eighth variant, the polymer according to the invention may comprise:
- a first block with a Tg of greater than or equal to 40° C., for example ranging from 60 to 90° C., which is an isobornyl acrylate/isobutyl methacrylate copolymer,
- a second block with a Tg of less than or equal to 20° C., for example ranging from −35 to −5° C., which is an isobutyl acrylate homopolymer, and
- an intermediate block which is an isobornyl acrylate/isobutyl methacrylate/isobutyl acrylate random copolymer.

The examples which follow illustrate, non-limitatively, polymers corresponding to this first embodiment.

The amounts are expressed in grams.

EXAMPLE 1

Preparation of a poly(isobornyl acrylate/methyl methacrylate/2-ethylhexyl acrylate) polymer 100 g of isododecane are introduced into a 1 liter reactor and then the temperature is raised so as to go from ambient temperature (25° C.) to 90° C. over 1 hour.

Subsequently there are added, at 90° C. and over 1 hour, 150 g of isobornyl acrylate, 60 g of methyl methacrylate, 110 g of isododecane and 1.8 g of 2,5-bis(2-ethylhexanoylperoxy)-2,5-dimethylhexane (Trigonox® 141 from Akzo Nobel).

The mixture is held at 90° C. for 1.5 h.

Subsequently there are introduced into the above mixture, still at 90° C. and over 30 minutes, 90 g of 2-ethylhexyl acrylate, 90 g of isododecane and 1.2 g of 2,5-bis(2-ethylhexanoylperoxy)-2,5-dimethylhexane.

The mixture is held at 90° C. for 3 hours and then the whole is cooled.

This gives a solution containing 50% polymer active substance in isododecane.

A polymer is obtained which comprises a first, poly(isobornyl acrylate/methyl methacrylate) block with a Tg of 100° C., a second, poly-2-ethylhexyl acrylate block with a Tg of −70° C., and an intermediate block which is an isobornyl acrylate/methyl methacrylate/2-ethylhexyl acrylate random polymer.

This polymer has a weight-average mass of 76 500 and a number-average mass of 22 000, giving a polydispersity index I of 3.48.

EXAMPLE 2

Preparation of a poly(isobornyl acrylate/isobornyl methacrylate/2-ethylhexyl acrylate) polymer 100 g of isododecane are introduced into a 1 liter reactor and then the temperature is raised so as to go from ambient temperature (25° C.) to 90° C. over 1 hour.

Subsequently there are added, at 90° C. and over 1 hour, 105 g of isobornyl acrylate, 105 g of isobornyl methacrylate, 110 g of isododecane and 1.8 g of 2,5-bis(2-ethylhexanoylperoxy)-2,5-dimethylhexane (Trigonox® 141 from Akzo Nobel).

The mixture is held at 90° C. for 1.5 h.

Subsequently there are introduced into the above mixture, still at 90° C. and over 30 minutes, 90 g of 2-ethylhexyl acrylate, 90 g of isododecane and 1.2 g of 2,5-bis(2-ethylhexanoylperoxy)-2,5-dimethylhexane.

The mixture is held at 90° C. for 3 hours and then the whole is cooled.

This gives a solution containing 50% polymer active substance in isododecane.

A polymer is obtained which comprises a first, poly(isobornyl acrylate/isobornyl methacrylate) block with a Tg of 110° C., a second, poly-2-ethylhexyl acrylate block with a Tg of −70° C., and an intermediate block which is an isobornyl acrylate/isobornyl methacrylate/2-ethylhexyl acrylate random polymer.

This polymer has a weight-average mass of 103 900 and a number-average mass of 21 300, giving a polydispersity index I of 4.89.

EXAMPLE 3

Preparation of a poly(isobornyl acrylate/isobutyl methacrylate/isobutyl acrylate) polymer 100 g of isododecane are introduced into a 1 liter reactor and then the temperature is raised so as to go from ambient temperature (25° C.) to 90° C. over 1 hour.

Subsequently there are added, at 90° C. and over 1 hour, 120 g of isobornyl acrylate, 90 g of isobutyl methacrylate, 110 g of isododecane and 1.8 g of 2,5-bis(2-ethylhexanoylperoxy)-2,5-dimethylhexane (Trigonox® 141 from Akzo Nobel).

The mixture is held at 90° C. for 1.5 h.

Subsequently there are introduced into the above mixture, still at 90° C. and over 30 minutes, 90 g of isobutyl acrylate, 90 g of isododecane and 1.2 g of 2,5-bis(2-ethylhexanoylperoxy)-2,5-dimethylhexane.

The mixture is held at 90° C. for 3 hours and then the whole is cooled.

This gives a solution containing 50% polymer active substance in isododecane.

A polymer is obtained which comprises a first, poly(isobornyl acrylate/isobutyl methacrylate) block with a Tg of 75° C., a second, polyisobutyl acrylate block with a Tg of −20° C., and an intermediate block which is an isobornyl acrylate/isobutyl methacrylate/isobutyl acrylate random polymer.

This polymer has a weight-average mass of 144 200 and a number-average mass of 49 300, giving a polydispersity index I of 2.93.

Second Embodiment

According to a second embodiment, the block polymer comprises a first block with a glass transition temperature (Tg) of between 20 and 40° C., in accordance with the blocks described in c), and a second block with a glass transition temperature of less than or equal to 20° C., as described above in b), or a glass transition temperature of greater than or equal to 40° C., as described in a) above.

Preferably the proportion of the first block with a Tg of between 20 and 40° C. ranges from 10% to 85%, better still from 30% to 80% and even better still from 50% to 70% by weight of the polymer.

When the second block is a block with a Tg of greater than or equal to 40° C., it is preferably present in a proportion ranging from 10% to 85% by weight, better still from 20% to 70% and even better still from 30% to 70% by weight of the polymer.

When the second block is a block with a Tg of less than or equal to 20° C., it is preferably present in a proportion ranging from 10% to 85% by weight, better still from 20% to 70% and even better still from 20% to 50% by weight of the polymer.

Preferably the first block with a Tg of between 20 and 40° C. is a copolymer obtained from monomers which are such that the corresponding homopolymer has a Tg of greater than or equal to 40° C., and from monomers which are such that the corresponding homopolymer has a Tg of less than or equal to 20° C.

Advantageously the second block with a Tg of less than or equal to 20° C. or with a Tg of greater than or equal to 40° C. is a homopolymer.

Thus, according to a first variant of this second embodiment, the block polymer may comprise:
- a first block with a Tg of between 20 and 40° C., for example with a Tg of 25 to 39° C., which is a copolymer comprising at least one methyl acrylate monomer, at least one methyl methacrylate monomer and at least one acrylic acid monomer,
- a second block with a Tg of greater than or equal to 40° C., for example ranging from 85 to 125° C., which is a homopolymer composed of methyl methacrylate monomers, and
- an intermediate block comprising at least one methyl acrylate or methyl methacrylate monomer, and
- an intermediate block comprising methyl methacrylate, at least one acrylic acid monomer and at least one methyl acrylate monomer.

According to a second variant of this second embodiment, the block polymer may comprise:
- a first block with a Tg of between 20 and 40° C., for example with a Tg of 21 to 39° C., which is a copolymer comprising isobornyl acrylate/isobutyl methacrylate/2-ethylhexyl acrylate,
- a second block with a Tg of less than or equal to 20° C., for example ranging from −65 to −35° C., which is a methyl methacrylate homopolymer, and
- an intermediate block which is an isobornyl acrylate/isobutyl methacrylate/2-ethylhexyl acrylate random copolymer.

According to a third variant of this second embodiment, the block polymer may comprise:
- a first block with a Tg of between 20 and 40° C., for example with a Tg of from 21 to 39° C., which is an isobornyl acrylate/methyl acrylate/acrylic acid copolymer,
- a second block with a Tg of greater than or equal to 40° C., for example ranging from 85 to 115° C., which is an isobornyl acrylate homopolymer, and
- an intermediate block which is an isobornyl acrylate/methyl acrylate/acrylic acid random copolymer.

The composition according to the invention contains preferably from 0.1% to 60% by weight of polymer active substance (or polymer solids), preferably from 0.5% to 50% by weight and more preferably from 1% to 40% by weight.

Film Former

The composition of the invention also includes at least one film former, which may be an organic or inorganic polymer. The film former, when it is an organic polymer, is not a film-forming ethylenic linear block polymer as described above.

In one embodiment, the film-forming organic polymer is at least one polymer selected from the group consisting of:

film-forming polymers which are soluble in the organic liquid medium, in particular fat-soluble polymers, when the organic liquid medium comprises at least one oil, film-forming polymers which are dispersible in the organic liquid solvent medium, in particular polymers in the form of non-aqueous dispersions of polymer particles, preferably dispersions in silicone oils or hydrocarbon-based oils; in one embodiment, the non-aqueous dispersions of polymer comprise polymer particles stabilized on their surface with at least one stabilizer, and are often referred to as "NADs" [non-aqueous dispersions], aqueous dispersions of particles of film-forming polymers, which are often known as "latices"; in this case, the composition should comprise an aqueous phase besides the organic liquid medium, water-soluble film-forming polymers; in this case, the composition should comprise an aqueous phase besides the organic liquid medium.

In one embodiment, the film former is a film-forming organic polymer which is soluble in the organic liquid medium.

I/ Polymers that are Soluble in the Organic Liquid Medium

When the organic liquid medium of the composition comprises at least one oil, the film former may be a polymer that is soluble in the the said oil. In this case, it is referred to as a fat-soluble polymer. The fat-soluble polymer may be of any chemical type and may especially be selected from:

a) fat-soluble, amorphous homopolymers and copolymers of olefins, of cycloolefins, of butadiene, of isoprene, of styrene, of vinyl ethers, esters or amides, or of (meth)acrylic acid esters or amides comprising a linear, branched or cyclic $C_4$-$C_{50}$ alkyl group, which are preferably amorphous. The preferred fat-soluble homopolymers and copolymers are obtained from monomers selected from the group consisting of isooctyl(meth)acrylate, isononyl(meth)acrylate, 2-ethylhexyl(meth)acrylate, lauryl(meth)acrylate, isopentyl(meth) acrylate, n-butyl(meth)acrylate, isobutyl(meth)acrylate, methyl(meth)acrylate, tert-butyl(meth)acrylate, tridecyl (meth)acrylate and stearyl(meth)acrylate, or mixtures thereof. Examples that will be mentioned include the alkyl acrylate/cycloalkyl acrylate copolymer sold by Phoenix Chem. under the name Giovarez AC-5099 ML, and vinylpyrrolidone copolymers, such as copolymers of a $C_2$ to $C_{30}$ alkene, such as a $C_3$ to $C_{22}$ alkene, and combinations thereof, may be used. As examples of VP copolymers that may be used in the invention, mention may be made of copolymers of VP/vinyl laurate, VP/vinyl stearate, butylated polyvinylpyrrolidone (PVP), VP/hexadecene, VP/triacontene or VP/acrylic acid/lauryl methacrylate.

Particular fat-soluble copolymers that may be mentioned include:

i) silicone-acrylic graft polymers having a silicone skeleton and acrylic grafts or having an acrylic skeleton and silicone grafts, such as the product sold under the name SA 70.5 by 3M and described in U.S. Pat. No. 5,725,882, U.S. Pat. No. 5,209,924, U.S. Pat. No. 4,972,037, U.S. Pat. No. 4,981,903, U.S. Pat. No. 4,981,902 and U.S. Pat. No. 5,468,477, and in U.S. Pat. No. 5,219,560 and EP 0 388 582;

ii) fat-soluble polymers belonging to one of the classes described above and bearing fluoro groups, in particular those described in U.S. Pat. No. 5,948,393 and the alkyl(meth) acrylate/perfluoroalkyl(meth)acrylate copolymers described in patents EP 0 815 836 and U.S. Pat. No. 5,849,318;

iii) polymers or copolymers resulting from the polymerization or copolymerization of an ethylenic monomer comprising one or more ethylenic, preferably conjugated, bonds (or dienes). As polymers or copolymers resulting from the polymerization or copolymerization of an ethylenic monomer, it is possible to use vinyl, acrylic or methacrylic copolymers.

In one embodiment, the film former is a block copolymer comprising at least one block composed of styrene units or styrene derivatives (for example methylstyrene, chlorostyrene or chloromethylstyrene). The copolymer comprising at least one styrene block may be a diblock or triblock copolymer, or even a multiblock copolymer, in starburst or radial form. The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, a methacrylate (MA) block or a combination of these blocks. The copolymer comprising at least one block composed of styrene units or styrene derivatives may be a triblock copolymer, and in particular of the polystyrene/polyisoprene or polystyrene/polybutadiene type, such as those sold or manufactured under the name "Luvitol HSB" by BASF, and those of the polystyrene/copoly(ethylene-propylene) type or alternatively of the polystyrene/copoly(ethylene-butylene) type, such as those sold or manufactured under the brand name "Kraton" by Shell Chemical Co. or Gelled Permethyl 99A by Penreco may be used. Styrene-methacrylate copolymers may also be used.

Copolymer comprising at least one block composed of styrene or styrene-derived units may be, for example, Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS), Kraton D-1107 (SIS), Gelled Permethyl 99A-750, Gelled Permethyl 99A-753-58 (blend of triblock polymer and of starburst block polymer), Gelled Permethyl 99A-753-59 (blend of triblock polymer and of starburst block polymer), Versagel 5970 and Versagel 5960 from Penreco (blend of triblock polymer and of starburst polymer in isododecane), and OS 129880, OS 129881 and OS 84383 from Lubrizol (styrene-methacrylate copolymer).

In one embodiment, the film former is selected from copolymers of a vinyl ester (the vinyl group being directly attached to the oxygen atom of the ester group and the vinyl ester having a saturated, linear or branched hydrocarbon-based radical of 1 to 19 carbon atoms, linked to the carbonyl of the ester group) and of at least one other monomer, which may be a vinyl ester (other than the vinyl ester already present), an α-olefin (containing from 8 to 28 carbon atoms), an alkyl vinyl ether (the alkyl group of which contains from 2 to 18 carbon atoms) or an allylic or methallylic ester (containing a saturated, linear or branched hydrocarbon-based radical of 1 to 19 carbon atoms, linked to the carbonyl of the ester group).

These copolymers may be partially crosslinked using crosslinking agents, which may be either of the vinyl type or of the allylic or methallylic type, such as tetraallyloxyethane, divinylbenzene, divinyl octanedioate, divinyl dodecanedioate, and divinyl octadecanedioate.

Examples of these copolymers that may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-di-methylpentanoate/vinyl laurate, vinyl dimethyl-propionate/vinyl stearate, allyl dimethylpropionate/vinyl stearate, vinyl propionate/vinyl stearate, crosslinked with 0.2% divinylbenzene, vinyl dimethyl-propionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Fat-soluble film-forming polymers that may also be mentioned include fat-soluble copolymers, and in particular those resulting from the copolymerization of vinyl esters containing from 9 to 22 carbon atoms or of alkyl acrylates or methacrylates, the alkyl radicals containing from 10 to 20 carbon atoms.

Such fat-soluble copolymers may be selected from copolymers of polyvinyl stearate, polyvinyl stearate crosslinked with divinylbenzene, with diallyl ether or with diallyl phthalate, polystearyl (meth)acrylate, polyvinyl laurate and polylauryl (meth)acrylate copolymers, these poly(meth)acrylates possibly being crosslinked with ethylene glycol dimethacrylate or tetraethylene glycol dimethacrylate.

The fat-soluble copolymers defined above are known and described especially in patent application FR-A-2 232 303; they may have a weight-average molecular weight ranging from 2000 to 500 000 and preferably from 4000 to 200 000.

As examples of fat-soluble polymers that may be used in the invention, mention may be made of poly-alkylenes and $C_2$-$C_{20}$ alkene copolymers, in particular polybutene.

b) amorphous and fat-soluble polycondensates, preferably not comprising any groups donating hydrogen interactions, in particular aliphatic polyesters having $C_{4-50}$ alkyl side chains or else polyesters resulting from the condensation of fatty acid dimers, or even polyesters comprising a silicone-based segment in the form of a block, graft or end group, which are solid at ambient temperature, as defined in patent application FR 0 113 920, not yet published.

c) amorphous and fat-soluble polysaccharides comprising alkyl (ether or ester) side chains, in particular alkylcelluloses containing a saturated or unsaturated, linear or branched $C_1$ to $C_8$ alkyl radical, such as ethylcellulose and propylcellulose.

The film-forming polymer may be selected in particular from cellulose-based polymers such as nitrocellulose, cellulose acetate, cellulose acetobutyrate, cellulose acetopropionate or ethylcellulose, or else from polyurethanes, acrylic polymers, vinyl polymers, polyvinyl butyrals, alkyd resins, resins derived from aldehyde condensation products, such as aryl-sulphonamide-formaldehyde resins, for instance toluenesulphonamide-formaldehyde resin, and aryl-sulphonamide epoxy resins.

Film-forming polymers that may especially be used include nitrocellulose RS ⅛ sec.; RS ¼ sec.; ½ sec.; RS 5 sec.; RS 15 sec.; RS 35 sec.; RS 75 sec.; RS 150 sec.; AS ¼ sec.; AS ½ sec.; SS ¼ sec.; SS ½ sec.; SS 5 sec., sold especially by the company Hercules; the toluenesulphonamide-formaldehyde resins "Ketjentflex MS80" from the company Akzo or "Santolite MHP" and "Santolite MS80" from the company Faconnier or "Resimpol 80" from the company Pan Americana, the alkyd resin "Beckosol Ode 230-70-E" from the company Dainippon, the acrylic resin "Acryloid B66" from the company-Rohm & Haas, and the polyurethane resin "Trixene PR 4127" from the company Baxenden.

d) silicone resins which are soluble or swellable by silicone oils. These resins are partially crosslinked polyorganosiloxanes which, depending on the degree of crosslinking, will be soluble or swellable by the silicone oils of the oily phase of the organic liquid medium. These silicone resins may be selected from the following non-limitative list: MQ resins or trimethylsiloxysilicates, polysilsesquioxanes or crosslinked dimethicone/vinyldimethicone polymers.

II/ Non-Aqueous Dispersions of Polymer Particles

The composition may contain a film former selected from non-aqueous dispersions of polymer particles. The particles are generally spherical. Before being incorporated into the composition of the invention, the particles are generally dispersed in a physiologically acceptable liquid fatty phase, such as hydrocarbon-based oils or silicone oils. According to one mode of implementation, these dispersions are generally known as NADs (non-aqueous dispersions) of polymer, as opposed to networks, which are aqueous dispersions of polymer. These dispersions may especially be in the form of nanoparticles of polymers in stable dispersion in the said fatty phase. In one embodiment the nanoparticles are between 5 nm and 600 nm in size. However, it is possible to obtain polymer particles ranging up to 1 μm in size.

One of the advantages of the polymer dispersion of the composition of the invention is the possibility of varying the glass transition temperature (Tg) of the polymer or the polymer system (polymer plus additive of the plasticizer type), and of thus going from a hard polymer to a more or less soft polymer, making it possible to adjust the mechanical properties of the composition depending on the intended application and in particular on the film deposited.

The polymers in dispersion which may be used in the composition of the invention preferably have a molecular weight ranging from about 2000 to 10 000 000 and a Tg ranging from −100° C. to 300° C. and better still from −50° C. to 50° C. and preferably from −10° C. to 100° C.

It is possible to use film-forming polymers, that preferably have a low Tg, of less than or equal to the temperature of the skin and especially less than or equal to 40° C. A dispersion is thus obtained which can form a film when it is applied to a support.

Among the film-forming polymers which may be mentioned are free-radical, acrylic or vinyl homopolymers or copolymers, preferably having a Tg of less than or equal to 40° C. and especially ranging from −10° C. to 30° C., used alone or as a mixture.

The expression "free-radical polymer" means a polymer obtained by polymerization of monomers containing unsaturation, especially ethylenic unsaturation, each monomer being capable of homo-polymerizing (unlike polycondensates). The free-radical polymers may especially be vinyl polymers or copolymers, especially acrylic polymers.

The vinyl polymers may result from the polymerization of ethylenically unsaturated monomers containing at least one acid group and/or esters of these acidic monomers and/or amides of these acids.

As monomers bearing an acidic group, it is possible to use α,β-ethylenic unsaturated carboxylic acids such as acrylic acid, methacrylic acid, crotonic acid, maleic acid or itaconic acid. (Meth)acrylic acid and crotonic acid are preferably used, and more preferentially (meth)acrylic acid.

The esters of acidic monomers are advantageously selected from the esters of (meth)acrylic acid (also known as (meth)acrylates), for instance alkyl (meth)acrylates, in particular of a $C_1$-$C_{20}$ and preferably a $C_1$-$C_6$ alkyl, aryl (meth)acrylates, in particular of a $C_6$-$C_{10}$ aryl, and hydroxyalkyl (meth)acrylates, in particular of a $C_2$-$C_6$ hydroxyalkyl. Alkyl (meth)acrylates which may be mentioned include methyl, ethyl, butyl, isobutyl, 2-ethylhexyl and lauryl (meth)acrylate. Hydroxyalkyl (meth)acrylates which may be mentioned include hydroxyethyl (meth)acrylate and 2-hydroxypropyl (meth)acrylate. Aryl (meth)acrylates which may be mentioned include benzyl or phenyl acrylate.

The (meth)acrylic acid esters that are particularly preferred are alkyl (meth)acrylates.

The free-radical polymers that are preferably used are copolymers of (meth)acrylic acid and of an alkyl (meth)acrylate, especially of a $C_1$-$C_4$ alkyl. More preferentially, methyl acrylates may be used, optionally copolymerized with acrylic acid.

The amides of the acidic monomers which may be mentioned include (meth)acrylamides, and especially N-alkyl (meth)acrylamides, in particular of a $C_2$-$C_{12}$ alkyl, such as N-ethylacrylamide, N-t-butylacrylamide and N-octylacrylamide; N-di($C_1$-$C_4$)alkyl(meth)acrylamides.

The vinyl film-forming polymers can result from the polymerization of monomers containing ethylenic unsaturation and containing at least one acidic group and/or esters of these acidic monomers and/or amides of these acidic monomers.

Monomers bearing an acidic group which may be used are α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously selected from (meth)acrylic acid esters (also known as (meth)acrylates), especially (meth)acrylates of an alkyl, in particular of a $C_1$-$C_{30}$ and preferably a $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

Among the alkyl (meth)acrylates that may be mentioned are methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl(meth)acrylates that may be mentioned are hydroxyethyl acrylate, 2-hydroxypropyl acrylate, hydroxyethyl methacrylate and 2-hydroxypropyl methacrylate.

Among the aryl (meth)acrylates that may be mentioned are benzyl acrylate and phenyl acrylate.

The (meth)acrylic acid esters that are particularly preferred are the alkyl (meth)acrylates.

According to the present invention, the alkyl group of the esters may be either fluorinated or perfluorinated, i.e. some or all of the hydrogen atoms of the alkyl group are substituted by fluorine atoms.

Examples of amides of the acidic monomers that may be mentioned are (meth)acrylamides, and especially N-alkyl (meth)acrylamides, in particular of a $C_2$-$C_{12}$ alkyl. Among the N-alkyl(meth)acrylamides that may be mentioned are N-ethylacrylamide, N-t-butylacrylamide, N-t-octylacrylamide and N-undecylacrylamide.

The vinyl film-forming polymers may also result from the homopolymerization or copolymerization of monomers selected from vinyl esters and styrenic monomers. In particular, these monomers may be polymerized with acidic monomers and/or esters thereof and/or amides thereof, such as those mentioned above.

Examples of vinyl esters that may be mentioned are vinyl acetate, vinyl neodecanoate, vinyl pivalate, vinyl benzoate and vinyl t-butylbenzoate.

Styrenic monomers that may be mentioned are styrene and alpha-methylstyrene.

In a non-limitative manner, the polymers in dispersion of the invention may be selected from the following polymers or copolymers: polyurethanes, polyurethane-acrylics, polyureas, polyurea-polyurethanes, polyester-polyurethanes, polyether-polyurethanes, polyesters, polyesteramides, fatty-chain polyesters, alkyds; acrylic and/or vinyl polymers or copolymers; acrylic-silicone copolymers; polyacrylamides; silicone polymers, for example silicone polyurethanes or silicone acrylics, and fluoro polymers, and mixtures thereof.

The polymer(s) in oily dispersion may represent (as solids or active substance) from 0.1% to 60%, preferably from 2% to 40% and better still from 4% to 25% of the weight of the composition. For a stabilizer that is solid at ambient temperature, the amount of solids in the dispersion represents the total amount of polymer and of stabilizer.

The fat-soluble or dispersible polymers in the composition of the invention may also be used in an amount ranging from 0.01% to 20% (as active substance), for instance from 1% to 10%, where appropriate, relative to the total weight of the composition.

III/ Aqueous Dispersions of Polymer Particles

According to another embodiment, the film-forming polymer may be selected from aqueous dispersions of polymer particles, in the case where the composition according to the invention comprises an aqueous phase.

The aqueous dispersion comprising one or more film-forming polymers may be prepared by a person skilled in the art on the basis of his or her general knowledge, especially by emulsion polymerization or by dispersion of the preformed polymer.

Among the film-forming polymers which may be used in the composition according to the present invention, mention may be made of synthetic polymers, of polycondensate type or of free-radical type, polymers of natural origin, and mixtures thereof.

Among the polycondensates, mention may thus be made of anionic, cationic, nonionic or amphoteric polyurethanes, polyurethane-acrylics, polyurethane-polyvinylpyrrolidones, polyester-polyurethanes, polyether-polyurethanes, polyureas, polyurea-polyurethanes, and mixtures thereof.

The polyurethanes may be, for example, an aliphatic, cycloaliphatic or aromatic polyurethane, polyurea/polyurethane or polyurea copolymer, containing, alone or as a mixture, at least one block of linear or branched aliphatic and/or cycloaliphatic and/or aromatic polyester origin, and/or at least one block of aliphatic and/or cycloaliphatic and/or aromatic polyether origin, and/or at least one substituted or unsubstituted, branched or unbranched silicone block, for example polydimethylsiloxane or polymethylphenylsiloxane, and/or at least one block comprising fluoro groups.

The polyurethanes as defined in the invention may also be obtained from branched or unbranched polyesters or from alkyds containing mobile hydrogens, which are modified by means of a polyaddition with a diisocyanate and a difunctional organic co-reactive compound (for example dihydro, diamino or hydroxyamino), also containing either a carboxylic acid or carboxylate group, or a sulphonic acid or sulphonate group, or alternatively a neutralizable tertiary amine group or a quaternary ammonium group.

Mention may also be made of polyesters, polyesteramides, fatty-chain polyesters, polyamides and epoxy ester resins.

The polyesters may be obtained, in a known manner, by polycondensation of aliphatic or aromatic diacids with aliphatic or aromatic diols or with polyols. Succinic acid, glutaric acid, adipic acid, pimelic acid, suberic acid or sebacic acid may be used as aliphatic diacids. Terephthalic acid or isophthalic acid, or alternatively a derivative such as phthalic anhydride, may be used as aromatic diacids. Ethylene glycol, propylene glycol, diethylene glycol, neopentyl glycol, cyclohexanedimethanol and 4,4-N-(1-methylpropylidene)bisphenol may be used as aliphatic diols. Glycerol, pentaerythritol, sorbitol and trimethylolpropane may be used as polyols.

The polyesteramides may be obtained in a similar manner to the polyesters, by polycondensation of diacids with diamines or amino alcohols. Ethylenediamine, hexamethylenediamine or meta- or para-phenylenediamine may be used as diamine. Monoethanolamine may be used as amino alcohol.

As monomer bearing an anionic group which may be used during the polycondensation, mention may be made, for example, of dimethylolpropionic acid, trimellitic acid or a derivative such as trimellitic anhydride, the sodium salt of pentanediol-3-sulphonic acid and the sodium salt of 5-sulpho-1,3-benzenedicarboxylic acid. The fatty-chain polyesters may be obtained using fatty-chain diols during the polycondensation. The epoxy ester resins may be obtained by polycondensation of fatty acids with a condensate having $\alpha,\omega$-diepoxy ends.

The free-radical polymers may in particular be acrylic and/or vinyl polymers or copolymers. Anionic radical polymers are preferred. As a monomer bearing an anionic group which may be used during the free-radical polymerization, mention may be made of acrylic acid, methacrylic acid, crotonic acid, maleic anhydride or 2-acrylamido-2-methylpropanesulphonic acid.

The acrylic polymers may result from the copolymerization of monomers selected from the esters and/or amides of acrylic acid or of methacrylic acid. As examples of monomers of ester type, mention may be made of methyl methacrylate, ethyl methacrylate, butyl methacrylate, isobutyl methacrylate, 2-ethylhexyl methacrylate and lauryl methacrylate. As examples of monomers of amide type, mention may be made of N-t-butylacrylamide and N-t-octylacrylamide.

Acrylic polymers obtained by copolymerization of ethylenically unsaturated monomers containing hydrophilic groups, preferably of nonionic nature, such as hydroxyethyl acrylate, 2-hydroxypropyl acrylate, hydroxyethyl methacrylate and 2-hydroxypropyl methacrylate, are preferably used.

The vinyl polymers may result from the homopolymerization or copolymerization of monomers selected from vinyl esters, styrene or butadiene. As examples of vinyl esters, mention may be made of vinyl acetate, vinyl neodecanoate, vinyl pivalate, vinyl benzoate and vinyl t-butylbenzoate.

Acrylic/silicone copolymers or even nitrocellulose/acrylic copolymers may also be used.

The polymers of natural origin, which are optionally modified, may be selected from shellac, sandarac gum, dammar resins, elemi gums, copal resins, cellulose derivatives, and mixtures thereof.

Mention may also be made of the polymers resulting from the free-radical polymerization of one or more free-radical monomers inside and/or partially at the surface of preexisting particles of at least one polymer selected from the group consisting of polyurethanes, polyureas, polyesters, polyesteramides and/or alkyds. These polymers are generally referred to as "hybrid polymers".

When an aqueous dispersion of polymer particles is used, the solids content of the the said aqueous dispersion may be from about 5% to 60% and preferably from 30% to 50% by weight.

The size of the polymer particles in aqueous dispersion may be between 10 and 500 nm and is preferably between 20 and 150 nm, allowing the production of a film of noteworthy gloss. However, particle sizes ranging up to 1 micron may be used.

Aqueous dispersions of film-forming polymers that may be used include the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ by the company Daito Kasey Kogyo; Syntran 5760 by the company Interpolymer or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulphopolyesters sold under the brand name Eastman AQ® by the company Eastman Chemical Products, and vinyl dispersions, for instance Mexomère PAM.

IV/ Water-Soluble Polymers

In the case where the composition comprises an aqueous phase, the film-forming polymer may be a water-soluble polymer. The water-soluble polymer is thus dissolved in the aqueous phase of the composition.

Among the water-soluble film-forming polymers that may be mentioned are the following cationic polymers:

(1) acrylic polymers or copolymers, such as polyacrylates or polymethacrylates; the copolymers of the family (1) may also contain one or more units derived from comonomers that may be selected from the family of acrylamides, methacrylamides, diacetone-acrylamides, acrylamides and methacrylamides substituted on the nitrogen by lower alkyls, acrylic or methacrylic acids or esters thereof, vinyllactams such as vinylpyrrolidone or vinylcaprolactam, or vinyl esters.

Thus, among these copolymers of the family (1), mention may be made of:

copolymers of acrylamide and of dimethylaminoethyl methacrylate, quaternized with dimethyl sulphate or with a dimethyl halide, such as the product sold under the name Hercofloc by the company Hercules, the copolymer of acrylamide and of methacryloyloxyethyltrimethylammonium chloride described, for example, in patent application EP-A-080 976 and sold under the name Bina Quat P 100 by the company Ciba Geigy, the copolymer of acrylamide and of methacryloyloxyethyltrimethylammonium methosulphate sold under the name Reten by the company Hercules, quaternized or non-quaternized copolymers of vinylpyrrolidone/dialkylaminoalkyl acrylate or methacrylate, such as the products sold under the name "Gafquat" by the company ISP, for instance "Gafquat 734" or "Gafquat 755", or alternatively the products denoted as "Copolymer 845, 958 and 937". These polymers are described in detail in French patents 2 077 143 and 2 393 573, terpolymers of dimethylaminoethyl methacrylate/vinylcaprolactam/vinylpyrrolidone, such as the product sold under the name Gaffix VC 713 by the company ISP; and the quaternized copolymer of vinyl-pyrrolidone/dimethylaminopropylmethacrylamide, such as the product sold under the name "Gafquat HS 100" by the company ISP;

(2) the quaternized polysaccharides described more particularly in U.S. Pat. No. 3,589,578 and U.S. Pat. No. 4,031,307, such as guar gums containing trialkyl-ammonium cationic groups. Such products are sold in particular under the trade names Jaguar C13 S, Jaguar C 15 and Jaguar C 17 by the company Meyhall;

(3) quaternary copolymers of vinylpyrrolidone and of vinylimidazole;

(4) chitosans or salts thereof;

(5) cationic cellulose derivatives such as copolymers of cellulose or of cellulose derivatives grafted with a water-soluble monomer comprising a quaternary ammonium, and described in particular in U.S. Pat. No. 4,131,576, such as hydroxyalkylcelluloses, for instance hydroxymethyl-, hydroxyethyl- or hydroxy-propylcelluloses grafted in particular with a methacryloyloxyethyltrimethylammonium, methacrylamidopropyltrimethylammonium or dimethyldiallylammonium salt. The products sold corresponding to this definition are, more particularly, the products sold under the name "Celquat L 200" and "Celquat H 100" by the National Starch Company.

Among the film-forming water-soluble polymers that may be mentioned are the following amphoteric polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamide and -acrylamide. Such compounds are described in U.S. Pat. No. 3,836,537;

(2) polymers comprising units derived from:
a) at least one monomer selected from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids, and the product of quaternization of dimethylaminoethyl methacrylate with dimethyl or diethyl sulphate;

(3) crosslinked alkylpolyaminoamides totally or partially derived from polyaminoamides;

(4) polymers comprising zwitterionic units;

(5) chitosan-derived polymer;

(6) polymers derived from the N-carboxy-alkylation of chitosan, such as N-carboxymethylchitosan or N-carboxybutylchitosan sold under the name "Evalsan" by the company Jan Dekker;

(7) ($C_1$-$C_5$)alkyl vinyl ether/maleic anhydride copolymers, partially modified by a semi-amidation with an N,N-dialkylaminoalkylamine, such as N,N-dimethyl-aminopropylamine, or by a semi-esterification with an N,N-dialkanolamine. These copolymers may also comprise other vinyl comonomers, such as vinylcaprolactam.

The water-soluble film-forming polymers are preferably selected from the group consisting of:
proteins, for instance proteins of plant origin, such as wheat proteins and soya proteins; proteins of animal origin, such as keratin, for example keratin hydrolysates and sulphonic keratins;

anionic, cationic, amphoteric or nonionic chitin or chitosan polymers;

cellulosic polymers, such as hydroxyethylcellulose, hydroxypropylcellulose, methylcellulose, ethylhydroxyethylcellulose and carboxymethylcellulose, and quaternized cellulose derivatives;

acrylic polymers or copolymers, such as polyacrylates or polymethacrylates;

vinyl polymers, for instance polyvinylpyrrolidones, copolymers of methyl vinyl ether and of maleic anhydride, the copolymer of vinyl acetate and of crotonic acid, copolymers of vinylpyrrolidone and of vinyl acetate;

copolymers of vinylpyrrolidone and of caprolactam; polyvinyl alcohols;

polymers of natural origin, which are optionally modified, such as:

gum arabic, guar gum, xanthan derivatives, karaya gum;
alginates and carrageenans;
glycosaminoglycans, hyaluronic acid and derivatives thereof;
shellac, sandarac gum, dammar resins, elemi gums and copal resins;
deoxyribonucleic acid;
mucopolysaccharides such as hyaluronic acid and chondroitin sulphate, and mixtures thereof.

These polymers will be used in particular if a more or less appreciable removal of the film by water is desired.

In order to improve the film-forming nature of an oily or aqueous polymer, it is possible to add to the polymer system a coalescer, which will be selected from the known coalescers.

According to one embodiment of the invention, the film-forming polymer may be selected from polymers containing a non-silicone organic skeleton grafted with monomers containing a polysiloxane. These polymers may be fat-soluble, lipodispersible, water-soluble or dispersible in aqueous medium, where appropriate.

The polymers containing a non-silicone organic skeleton grafted with monomers containing a polysiloxane consist of an organic main chain formed from organic monomers not comprising silicone, onto which is grafted, within the said chain and also optionally on at least one of its ends, at least one polysiloxane macromer.

In the text hereinbelow, in accordance with what is generally accepted, the expression "polysiloxane macromer" is understood to refer to any monomer containing a polysiloxane-type polymer chain in its structure.

The non-silicone organic monomers constituting the main chain of the grafted silicone polymer can be selected from free-radically polymerizable monomers containing ethylenic unsaturation, polycondensation-polymerizable monomers, such as those forming polyamides, polyesters or polyurethanes, and ring-opening monomers, such as those of the oxazoline or caprolactone type.

The polymers containing a non-silicone organic skeleton grafted with monomers containing a polysiloxane, in accordance with the present invention, can be obtained according to any means known to those skilled in the art, in particular by reaction between (i) a starting polysiloxane macromer which is correctly functionalized on the polysiloxane chain and (ii) one or more non-silicone organic compounds, themselves correctly functionalized with a function which is capable of reacting with the functional group(s) borne by the said silicone, forming a covalent bond; a classic example of such a reaction is the free-radical reaction between a vinyl group borne on one of the ends of the silicone with a double bond of a monomer containing ethylenic unsaturation in the main chain.

The polymers containing a non-silicone organic skeleton grafted with monomers containing a polysiloxane, in accordance with the invention, are more preferably selected from those described in U.S. Pat. No. 4,693,935, U.S. Pat. No. 4,728,571 and U.S. Pat. No. 4,972,037 and patent applications EP-A-0 412 704, EP-A-0 412 707, EP-A-0 640 105 and WO 95/00578. These are copolymers obtained by free-radical polymerization starting with monomers containing ethylenic unsaturation and monomers having a terminal vinyl group, or alternatively copolymers obtained by reaction of a polyolefin comprising functionalized groups and a polysiloxane macromer having a terminal function which is reactive with the said functionalized groups.

One particular family of grafted silicone polymers which is suitable for carrying out the present invention consists of grafted silicone polymers comprising:

a) from 0% to 98% by weight of at least one free-radically polymerizable lipophilic monomer (A) of low polarity containing ethylenic unsaturation;

b) from 0% to 98% by weight of at least one polar hydrophilic monomer (B) containing ethylenic unsaturation, which is copolymerizable with the monomer(s) of the type (A);

c) from 0.01% to 50% by weight of at least one polysiloxane macromer (C) of general formula:

$$X(Y)_n Si(R)_{3-m} Z_m \qquad (I)$$

in which:
X denotes a vinyl group which is copolymerizable with the monomers (A) and (B);
Y denotes a divalent bonding group;
R denotes hydrogen, $C_1$-$C_6$ alkyl or alkoxy, or $C_6$-$C_{12}$ aryl;
Z denotes a monovalent polysiloxane unit with a number-average molecular weight of at least 500;
n is 0 or 1 and m is an integer ranging from 1 to 3;
the percentages being calculated relative to the total weight of the monomers (A), (B) and (C).

These polymers have a number-average molecular weight ranging from 10 000 to 2 000 000 and preferably a glass transition temperature Tg or a crystalline melting temperature Tm of at least −20° C.

As examples of lipophilic monomers (A), mention may be made of acrylic or methacrylic acid esters of $C_1$-$C_{18}$ alcohols; methacrylic acid esters of $C_{12}$-$C_{30}$ alcohols, styrene; polystyrene macromers; vinyl acetate; vinyl propionate; alpha-methylstyrene; tert-butylstyrene; butadiene; cyclohexadiene; ethylene; propylene; vinyltoluene; acrylic or methacrylic acid esters of 1,1-dihydroperfluoroalkanols or of homologues thereof; acrylic or methacrylic acid esters of omega-hydrofluoroalkanols; acrylic or methacrylic acid esters of fluoroalkylsulphonamido alcohols; acrylic or methacrylic acid esters of fluoroalkyl alcohols; acrylic or methacrylic acid esters of fluoroether alcohols; or mixtures thereof. The preferred monomers (A) are selected from the group consisting of n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)ethyl acrylate and 2-(N-butylperfluorooctanesulphonamido)ethyl acrylate, and mixtures thereof.

As examples of polar monomers (B), mention may be made of acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and hemiesters thereof, hydroxyalkyl (meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinylcaprolactam, or mixtures thereof. The preferred monomers (B) are selected from the group consisting of acrylic acid, N,N-dimethylacrylamide, dimethylaminoethyl methacrylate, quaternized dimethylaminoethyl methacrylate and vinylpyrrolidone, and mixtures thereof.

Mention is made especially of the product KP 561 or KP 562 sold by Shin Etsu such that the monomer (A) is selected from esters of a $C_{18}$-$C_{22}$ alcohol and of methacrylic acid.

The polysiloxane macromers (C) of formula (I) are selected preferably from those corresponding to the general formula (II) below:

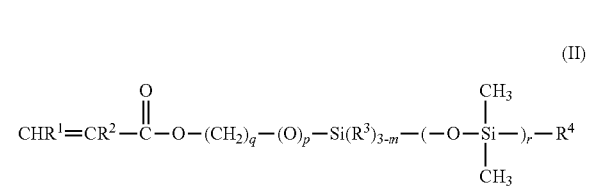

(II)

in which:
$R^1$ is hydrogen or —COOH (preferably hydrogen);
$R^2$ is hydrogen, methyl or —CH$_2$COOH (preferably methyl);
$R^3$ is $C_1$-$C_6$ alkyl, alkoxy or alkylamino, $C_6$-$C_{12}$ aryl or hydroxyl (preferably methyl);
$R^4$ is $C_1$-$C_6$ alkyl, alkoxy or alkylamino, $C_6$-$C_{12}$ aryl or hydroxyl (preferably methyl);
q is an integer from 2 to 6 (preferably 3);
p is 0 or 1;
r is an integer from 5 to 700;
m is an integer from 1 to 3 (preferably 1).

Preference is given to using the polysiloxane macromers of formula:

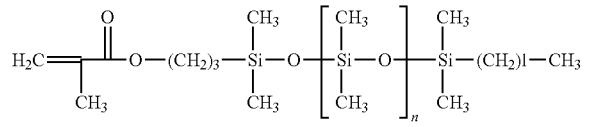

with n being a number ranging from 5 to 700 and 1 being an integer between 0 and 3.

One embodiment of the invention consists in using a copolymer which may be obtained by free-radical polymerization starting from the monomer mixture consisting of:
a) 60% by weight of tert-butyl acrylate;
b) 20% by weight of acrylic acid;
c) 20% by weight of silicone macromer of formula:

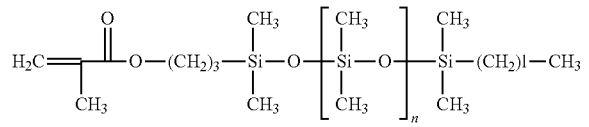

with n being a number ranging from 5 to 700 and 1 being an integer between 0 and 3, the weight percentages being calculated relative to the total weight of the monomers.

Another particular embodiment of the invention consists in using a copolymer which may be obtained by free-radical polymerization starting from the monomer mixture consisting of:

a) 80% by weight of tert-butyl acrylate;
b) 20% by weight of silicone macromer of formula:

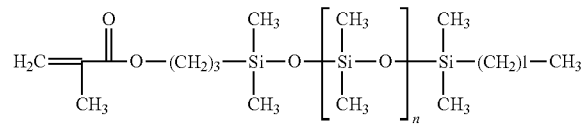

with n being a number ranging from 5 to 700 and 1 being an integer between 0 and 3, the weight percentages being calculated relative to the total weight of the monomers.

Another particular family of grafted silicone polymers containing a non-silicone organic skeleton that is suitable for carrying out the present invention consists of grafted silicone copolymers which may be obtained by reactive extrusion-moulding of a polysiloxane macromer with a reactive terminal function on a polymer of the polyolefin type comprising reactive groups capable of reacting with the terminal function of the polysiloxane macromer to form a covalent bond for grafting the silicone onto the main chain of the polyolefin. These polymers are described, along with a process for their preparation, in patent application WO 95/00578.

The reactive polyolefins are preferably selected from polyethylenes and polymers of ethylene-derived monomers such as propylene, styrene, alkylstyrene, butylene, butadiene, (meth)acrylates, vinyl esters or equivalents, comprising reactive functions capable of reacting with the terminal function of the polysiloxane macromer. They are selected more particularly from copolymers of ethylene or of ethylene derivatives and of monomers selected from those comprising a carboxylic function such as (meth)acrylic acid; those comprising an acid anhydride function such as maleic anhydride; those comprising an acid chloride function such as (meth)acryloyl chloride; those comprising an ester function such as (meth)acrylic acid esters; those comprising an isocyanate function.

The silicone macromers are preferably selected from polysiloxanes comprising a functionalized group, at the end of the polysiloxane chain or close to the end of the said chain, selected from the group consisting of alcohols, thiols, epoxy groups and primary and secondary amines, and more particularly from those corresponding to the general formula:

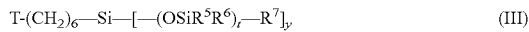

in which T is selected from the group consisting of $NH_2$, NHRN and an epoxy, OH, or SH function; $R^5$, $R^6$, $R^7$ and RN independently denote a $C_1$-$C_6$ alkyl, phenyl, benzyl, or $C_6$-$C_{12}$ alkylphenyl or hydrogen; s is a number from 2 to 100; t is a number from 0 to 1000 and y is a number from 1 to 3. They have a number-average molecular weight preferably ranging from 5000 to 300 000, more preferably from 8000 to 200 000 and more particularly from 9000 to 40 000.

According to one preferred embodiment, the film-forming polymer may be purchased from the Minnesota Mining and Manufacturing Company under the trade names of "Silicone Plus" polymers. For example, poly(isobutyl methacrylate-co-methyl FOSEA)-g-poly(dimethylsiloxane) is sold under the trade name SA 70-5 IBMMF.

According to another preferred form of the invention, the film-forming polymer is selected from silicone polymers grafted with non-silicone organic monomers. These polymers may be fat-soluble, fat-dispersible, water-soluble or dispersible in aqueous medium, where appropriate.

The said grafted silicone polymer(s) containing a polysiloxane skeleton grafted with non-silicone organic monomers comprise a silicone (or polysiloxane (/SiO—)$_n$) main chain onto which is grafted, within the said chain and also optionally on at least one of its ends, at least one organic group not comprising silicone.

The polymers containing a polysiloxane skeleton grafted with non-silicone organic monomers, according to the invention, can be existing commercial products or alternatively can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between /Si—H groups and vinyl groups $CH_2$=CH—, or alternatively the reaction between thio functional groups —SH with these same vinyl groups.

Examples of polymers containing a polysiloxane skeleton grafted with non-silicone organic monomers that are suitable for carrying out the present invention, and also their specific mode of preparation, are described in particular in patent applications EP-A-0 582 152, WO 93/23009 and WO 95/03776, the teachings of which are included in their entirety in the present description by way of non-limitative references.

According to a particularly preferred embodiment of the present invention, the silicone polymer containing a polysiloxane skeleton grafted with non-silicone organic monomers which is used comprises the result of a free-radical copolymerization between, on the one hand, at least one non-silicone anionic organic monomer containing ethylenic unsaturation and/or a non-silicone hydrophobic organic monomer containing ethylenic unsaturation, and, on the other hand, a silicone containing in its chain at least one, and preferably several, functional group(s) capable of reacting with the said ethylenic unsaturations of the said non-silicone monomers, forming a covalent bond, in particular thio functional groups.

According to the present invention, the said anionic monomers containing ethylenic unsaturation are preferably selected, alone or as mixtures, from linear or branched, unsaturated carboxylic acids, optionally partially or totally neutralized in the form of a salt, it being possible for this or these unsaturated carboxylic acid(s) to be, more particularly, acrylic acid, methacrylic acid, maleic acid, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the free-radical (homo)polymerization of at least one anionic monomer of unsaturated carboxylic acid type can, after reaction, be post-neutralized with a base (sodium hydroxide, aqueous ammonia, etc.) in order to turn it into a salt.

According to the present invention, the hydrophobic monomers containing ethylenic unsaturation are preferably selected, alone or as mixtures, from acrylic acid esters of alkanols and/or methacrylic acid esters of alkanols. The alkanols are preferably $C_1$-$C_{30}$ and more particularly $C_1$-$C_{22}$. The preferred monomers are selected from the group consisting of isooctyl(meth)acrylate, isononyl(meth)acrylate, 2-ethylhexyl(meth)acrylate, lauryl(meth)acrylate, isopentyl(meth)acrylate, n-butyl(meth)acrylate, isobutyl(meth)acrylate, methyl(meth)acrylate, tert-butyl(meth)acrylate, tridecyl(meth)acrylate and stearyl(meth)acrylate, or mixtures thereof.

One family of silicone polymers containing a polysiloxane skeleton grafted with non-silicone organic monomers that is particularly suitable for carrying out the present invention consists of silicone polymers comprising in their structure the unit of formula IV below:

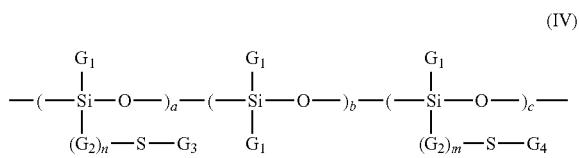

in which the radicals $G_1$, which are identical or different, represent hydrogen, a $C_1$-$C_{10}$ alkyl radical or a phenyl radical; the radicals $G_2$, which may be identical or different, represent a $C_1$-$C_{10}$ alkylene group; $G_3$ represents a polymer residue resulting from the (homo)polymerization of at least one anionic monomer containing ethylenic unsaturation; $G_4$ represents a polymer residue resulting from the (homo)-polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (IV) of the above text has at least one, and even more preferably all, of the following characteristics:
- the radicals $G_1$ denote an alkyl radical, preferably a methyl radical;
- n is not zero, and the radicals $G_2$ represent a divalent $C_1$-$C_3$ radical, preferably a propylene radical;
- $G_3$ represents a polymer radical resulting from the (homo) polymerization of at least one monomer of the carboxylic acid type containing ethylenic unsaturation, preferably acrylic acid and/or methacrylic acid;
- $G_4$ represents a polymer radical resulting from the homo polymerization of at least one monomer of the $C_1$-$C_{10}$ alkyl (meth)acrylate type, preferably isobutyl or methyl (meth)acrylate.

Examples of silicone polymers corresponding to the formula (IV) are, in particular, polydimethylsiloxanes (PDMSs) onto which are grafted, via a thiopropylene-type connecting chain, mixed polymer units of the poly(meth)acrylic acid type and of the polyalkyl (meth)acrylate type.

Other examples of silicone polymers corresponding to formula (IV) are, in particular, polydimethylsiloxanes (PDMSs) onto which are grafted, via a thiopropylene-type connecting chain, polymer units of the polyisobutyl (meth)acrylate type.

Such polymers include polymers comprising at least one group of formula:

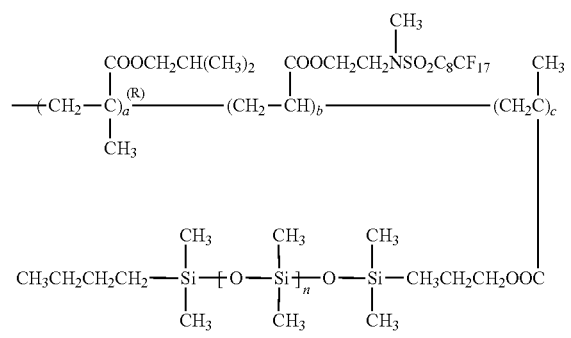

in which
a, b and c, which may be identical or different, are each a number ranging from 1 to 100 000; and the end groups, which may be identical or different, are each selected from linear $C_1$-$C_{20}$ alkyl groups, $C_3$-$C_{20}$ branched-chain alkyl groups, $C_3$-$C_{20}$ aryl groups, linear $C_1$-$C_{20}$ alkoxy groups and branched $C_3$-$C_{20}$ alkoxy groups.

Such polymers are disclosed in U.S. Pat. Nos. 4,972,037, 5,061,481, 5,209,924, 5,849,275, 6,033,650 and WO 93/23446 and WO 95/06078.

Another family of silicone polymers having a polysiloxane skeleton grafted with non-silicone organic monomers, which is particularly suitable for performing the present invention, consists of silicone polymers comprising in their structure the unit of formula (V) below:

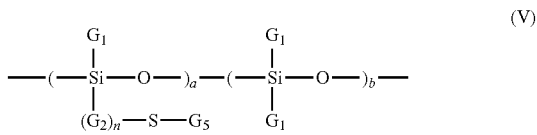

in which the radicals $G_1$ and $G_2$ have the same meaning as above; $G_5$ represents a polymer residue resulting from the (homo)polymerization of at least one ethylenically unsaturated hydrophobic monomer or from the copolymerization of at least one ethylenically unsaturated anionic monomer and of at least one ethylenically unsaturated hydrophobic monomer; n is equal to 0 or 1; a is an integer ranging from 0 to 50; b is an integer that may be between 10 and 350; on condition that a is other than 0.

The unit of formula (V) in the above text preferably has at least one, and even more preferably all, of the following characteristics:
- the radicals $G_1$ denote an alkyl radical, preferably a methyl radical;
- n is not zero, and the radicals $G_2$ represent a $C_1$-$C_3$ divalent radical, preferably a propylene radical.

The number-average molecular mass of the silicone polymers with a polysiloxane skeleton grafted with non-silicone organic monomers of the invention preferably ranges from about 10 000 to 1 000 000 and even more preferably from about 10 000 to 100 000.

The composition may contain from 2% to 60% by weight, better still from 5% to 60% and preferably from 2% to 30% by weight of solids of film-forming polymer. More generally, the total amount of polymer should be an amount sufficient to form on the skin and/or the lips a cohesive film capable of following the movements of the skin and/or the lips without becoming detached or cracking.

When the polymer has a glass transition temperature that is too high for the desired use, a plasticizer may be combined therewith so as to lower this temperature of the mixture used. The plasticizer may be selected from the plasticizers usually used in the field of application, and especially from compounds that can be solvents for the polymer.

The composition according to the invention may comprise a hydrophilic medium comprising water or a mixture of water and hydrophilic organic solvent(s), for instance alcohols, and especially linear or branched lower monoalcohols having 2 to 5 carbon atoms, such as ethanol, isopropanol or n-propanol, and polyols such as glycerol, diglycerol, propylene glycol, sorbitol, pentylene glycol, and polyethylene glycols, or else $C_2$ ethers and $C_2$-$C_4$ aldehydes which are hydrophilic.

The water or mixture of water and hydrophilic organic solvents may be present in the composition according to the invention in an amount ranging from 0.1% to 99% by weight, relative to the total weight of the composition, and preferably from 10% to 80% by weight.

The composition according to the invention may comprise emulsifying surfactants, which are present particularly in a proportion ranging from 2% to 30% by weight, relative to the total weight of the composition, and better still from 5% to 15%. These surfactants may be selected from anionic and nonionic surfactants. Reference may be made to the document "Encyclopaedia of Chemical Technology, Kirk-Othmer", volume 22, pp. 333-432, 3rd edition, 1979, Wiley, for the definition of the properties and functions (emulsifying) of the surfactants, especially pp. 347-77 of the said reference, for the anionic and nonionic surfactants.

The surfactants used preferentially in the composition according to the invention are selected:
  from nonionic surfactants: fatty acids, fatty alcohols, polyethoxylated and polyglycerolated fatty alcohols, such as polyethoxylated stearyl or cetylstearyl alcohols, fatty acid esters of sucrose, alkyl glucose esters, especially the polyoxyethylenated fatty esters of $C_1$-$C_6$ alkyl glucose, and mixtures thereof.
  from anionic surfactants: $C_{16}$-$C_{30}$ fatty acids neutralized with amines, aqueous ammonia or alkali metal salts, and mixtures thereof.

According to one embodiment it is preferred to use surfactants which allow an oil-in-water or wax-in-water emulsion to be obtained.

The composition according to the invention comprises an organic liquid medium which is cosmetically acceptable (acceptable tolerance, toxicology and feel).

According to one particularly preferred embodiment the organic liquid medium of the composition comprises at least one organic solvent, which is the, or one of the, polymerization solvent(s) of the block polymer as described above. Advantageously the said organic solvent is the majority liquid by weight in the organic liquid medium of the cosmetic composition.

According to one embodiment, the organic solvent medium comprises fatty substances which are liquid at ambient temperature (25° C. in general), called oils. These liquid fatty substances may be animal, vegetable, mineral or synthetic in origin.

As oils which can be used in the invention mention may be made of: hydrocarbon oils of animal origin, such as perhydrosqualene; vegetable hydrocarbon oils, such as liquid triglycerides of fatty acids of 4 to 10 carbon atoms, such as heptanoic or octanoic acid triglycerides, or else sunflower oil, corn oil, soya oil, grape seed oil, sesame oil, apricot oil, macadamia oil, castor oil, avocado oil, caprylic/capric acid triglycerides, jojoba oil, karite butter; linear or branched hydrocarbons, of mineral or synthetic origin, such as liquid paraffins and derivatives thereof, Vaseline, polydecenes, hydrogenated polyisobutene such as parleam; the synthetic esters and ethers particularly of fatty acids, such as, for example, purcellin oil, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, and heptanoates, octanoates and decanoates of fatty alcohols; polyol esters such as propylene glycol dioctanoate, neopentyl glycol diheptanoate and diethylene glycol diisononanoate; and pentaerythritol esters; fatty alcohols having 12 to 26 carbon atoms, such as octyldodecanol, 2-butyloctanol, 2-hexyldecanol, 2-undecylpentadecanol, and oleyl alcohol; partially hydrocarbon-based and/or silicone-based fluoro oils; silicone oils, such as volatile or non-volatile polydimethylsiloxanes (PDMS) that are linear or cyclic, such as cyclomethicones, dimethicones, optionally including a phenyl group, such as phenyl trimethicones, phenyltrimethylsiloxydiphenylsiloxanes, diphenylmethyldimethyltrisiloxanes, diphenyldimethicones, phenyldimethicones and polymethylphenylsiloxanes; and mixtures thereof.

These oils may be present in an amount ranging from 0.01% to 90%, and better still from 0.1% to 85% by weight, relative to the total weight of the composition.

The organic liquid medium of the composition according to the invention may also comprise one or more organic solvents which are cosmetically acceptable (acceptable tolerance, toxicology and feel).

These solvents may be generally present in an amount ranging from 0.1% to 90%, more preferably from 10% to 90% by weight, relative to the total weight of the composition, and better still from 30% to 90%.

As solvents which can be used in the composition of the invention mention may be made, besides the aforementioned hydrophilic organic solvents, of ketones which are liquid at ambient temperature, such as methyl ethyl ketone, methyl isobutyl ketone, diisobutyl ketone, isophorone, cyclohexanone and acetone; propylene glycol ethers which are liquid at ambient temperature, such as propylene glycol monomethyl ether, propylene glycol monomethyl ether acetate, and dipropylene glycol mono-n-butyl ether; short-chain esters (having 3 to 8 carbon atoms in total), such as ethyl acetate, methyl acetate, propyl acetate, n-butyl acetate and isopentyl acetate; ethers which are liquid at ambient temperature, such as diethyl ether, dimethyl ether or dichlorodiethyl ether; alkanes which are liquid at ambient temperature, such as decane, heptane, dodecane, isododecane and cyclohexane; aromatic cyclic compounds which are liquid at ambient temperature, such as toluene and xylene; and aldehydes which are liquid at ambient temperature, such as benzaldehyde and acetaldehyde, and mixtures thereof.

The composition according to the invention may include at least one wax. By wax in the sense of the present invention is meant a lipophilic compound which is solid at ambient temperature (25° C.), exhibits a reversible solid/liquid state change and has a melting point greater than or equal to 30° C. and possibly up to 120° C.

The melting point of the wax can be measured by means of a differential scanning calorimeter (DSC), an example being the calorimeter sold under the name DSC 30 by the company Mettler.

The waxes may be hydrocarbon waxes, fluoro waxes and/or silicone waxes and may be vegetable, mineral, animal and/or synthetic in origin. In particular the waxes have a melting point of more than 25° C. and better still more than 45° C.

As wax which can be used in the composition of the invention mention may be made of beeswax, carnauba wax or candelilla wax, paraffin, microcrystalline waxes, ceresin or ozokerite; synthetic waxes such as polyethylene waxes or Fischer-Tropsch waxes, and silicone waxes such as the alkyl- or alkoxy-dimethicones having 16 to 45 carbon atoms.

The gums are generally high molecular weight polydimethylsiloxanes (PDMS) or cellulose gums or polysaccharides. The pasty substances are generally hydrocarbon compounds such as lanolins and their derivatives or else PDMS.

The nature and amount of the solid fatty substances are a function of the desired mechanical properties and textures. By way of indication the composition may contain from 0% to 50% by weight of waxes, relative to the total weight of the composition, and better still from 1% to 30% by weight. The polymer may be combined with one or more auxiliary film-forming agents. A film-forming agent of this kind may be selected from all of the compounds known to the person skilled in the art as being capable of fulfilling the desired function, and particularly may be selected from plasticizers and coalescers.

The composition according to the invention may further comprise one or more colorants selected from water-soluble dyes and pulverulent colorants such as pigments, nacres and flakes, which are well known to the person skilled in the art. The colorants may be present in the composition in an amount ranging from 0.01% to 50% by weight, relative to the weight of the composition, preferably from 0.01% to 30% by weight.

By pigments are meant particles of any form, white or coloured, organic or inorganic, which are insoluble in the physiological medium and are intended for colouring the composition.

By nacres are meant iridescent particles of any form that are produced in particular by certain molluscs in their shell, or else are synthesized.

The pigments may be white or coloured, organic and/or inorganic. Among inorganic pigments mention may be made of titanium dioxide, optionally in surface-treated form, zirconium oxide or cerium oxide, and also zinc oxide, iron oxides (black, yellow or red) or chromium oxide, manganese violet, ultramarine blue, chromium hydrate and ferric blue, and metal powders such as aluminium powder and copper powder.

Among organic pigments mention may be made of carbon black, D & C pigments, and the cochineal carmine-based lakes of barium, strontium, calcium and aluminium.

Mention may also be made of effect pigments, such as particles comprising an organic or inorganic, natural or synthetic substrate, for example glass, acrylic resins, polyester, polyurethane, polyethylene terephthalate, ceramics or aluminas, the said substrate being uncovered or covered with metallic substances such as aluminium, gold, silver, platinum, copper or bronze, or with metal oxides such as titanium dioxide, iron oxide or chromium oxide, and mixtures thereof.

The nacreous pigments may be selected from white nacreous pigments such as titanium-covered mica, or bismuth oxychloride, coloured nacreous pigments such as titanium mica covered with iron oxides, titanium mica covered with, in particular, ferric blue or chromium oxide, titanium mica covered with an organic pigment of the aforementioned type, and also nacreous pigments based on bismuth oxychloride. It is also possible to use interference pigments, especially those which are liquid-crystal pigments or multi-layer pigments.

The water-soluble dyes are, for example, beetroot juice and methylene blue.

The composition according to the invention may further comprise one or more fillers, particularly in an amount ranging from 0.01% to 50% by weight, relative to the total weight of the composition, preferably ranging from 0.01% to 30% by weight. By fillers are meant particles of any form, colourless or white, mineral or synthetic, which are insoluble in the medium of the composition irrespective of the temperature at which the composition is manufactured. These fillers serve in particular to modify the rheology or texture of the composition.

The fillers may be organic or inorganic and may be in any form, platelet-shaped, spherical or oblong, irrespective of the crystallographic form (for example leaf, cubic, hexagonal, orthorhombic, etc.). Mention may be made of talc, mica, silica, kaolin, polyamide (Nylon®) powders (Orgasol® from Atochem), poly-β-alanine and polyethylene, the powders of polymers of tetrafluoroethylene (Teflon®), lauroyl-lysine, starch, boron nitride, hollow polymeric microspheres such as those of polyvinylidene chloride/acrylonitrile, for instance Expancel® (Nobel Industrie), acrylic acid copolymers (Polytrap® from the company Dow Corning) and silicone resin microbeads (Tospearls® from Toshiba, for example), elastomeric polyorganosiloxane particles, precipitated calcium carbonate, magnesium carbonate and magnesium hydrocarbonate, hydroxyapatite, hollow silica microspheres (Silica Beads® from Maprecos), ceramic or glass microcapsules, metal soaps derived from organic carboxylic acids having 8 to 22 carbon atoms, preferably 12 to 18 carbon atoms, for example zinc stearate, magnesium stearate or lithium stearate, zinc laurate and magnesium myristate.

The composition according to the invention may be in the form in particular of a stick, suspension, dispersion, solution, gel, emulsion, especially oil-in-water (O/W) or water-in-oil (W/O), or multiple (O/W/O or polyol/O/W or W/O/W), emulsion, or in the form of a cream, paste or mousse, or a vesicle dispersion, particularly of ionic or nonionic lipids, or a two-phase or multi-phase lotion, a spray, powder or paste, especially a flexible paste (in particular a paste having a dynamic viscosity at 25° C. of the order of 0.1 to 40 Pa·s at a shear rate of 200 s$^{-1}$, after 10 minutes of measurement in cone/plate geometry). The composition may be anhydrous: for example, it may be an anhydrous paste.

The person skilled in the art will be able to select the appropriate type of formulation, and the method of preparing it, on the basis of his or her general knowledge, taking into account, on the one hand, the nature of the constituents used, and especially their solubility in the vehicle, and, on the other hand, the application envisaged for the composition.

The composition according to the invention may be a makeup composition such as products for the complexion (foundations), rouges, eyeshadows, lipsticks, concealers, blushers, mascaras, eyeliners, eyebrow makeup products, lip pencils, eye pencils, nail products, such as nail varnishes, body makeup products or hair makeup products (hair lacquer or mascara).

The composition according to the invention may also be a facial or bodily skincare product, in particular a sun product or skin colouring product (such as a self-tanning product).

The composition according to the invention may also be a hair product, particularly a product for maintaining the hairstyle or the shaping of the hair. The hair compositions are preferably shampoos, gels, setting lotions, styling lotions, fixing compositions and styling compositions such as lacquers or sprays.

According to one embodiment the invention provides a coating composition for keratin fibres (such as the eyelashes, eyebrows and hair) comprising an organic liquid medium, at least one aqueous phase and at least one film-forming ethylenic linear block polymer and a dispersion of particles of film-forming polymer as described above.

Advantageously the water-dispersible film-forming polymer is selected from polyurethanes, polyurethane-acrylics, polyacrylics, poly(meth)acrylic esters, polyvinylpyrrolidones, polyurethane-polyvinylpyrrolidones, polyester-polyurethanes, polyether-polyurethanes, polyureas, polyurea/polyurethanes, and mixtures thereof as defined above.

Advantageously the composition comprises at least one second film former selected from water-soluble polymers such as cationic cellulose derivatives and/or optionally modified polymers of natural origin such as gum arabic.

Preferably the said composition comprises a wax, and more preferably it comprises a surfactant.

A composition of this kind may be present in a variety of forms: for example, in the form of two-phase wax-in-water or water-in-wax emulsions, or aqueous or anhydrous dispersions.

Advantageously the composition is a composition for coating the lashes, or mascara.

The present invention likewise provides a cosmetic kit comprising:
- a container delimiting at least one compartment, the said container being closed by a closing element; and
- a composition as described above disposed inside the said compartment.

The container may be in any appropriate form. It may in particular be in the form of a bottle, tube, jar, case, box, sachet or carton.

The closing element may be in the form of a removable stopper, a lid, a cap, a tear-off strip or a capsule, particularly of the type comprising a body attached to the container and a cover cap articulated on the body. It may also be in the form of an element for selectively closing the container, particularly a pump, valve or valve flap.

The container may be combined with an applicator, particularly in the form of a brush comprising an arrangement of bristles held by a twisted wire. A twisted brush of this kind is described in particular in U.S. Pat. No. 4,887,622. It may also be in the form of a comb comprising a plurality of application elements, obtained in particular from moulding. Combs of this kind are described, for example, in patent FR 2 796 529. The applicator may be in the form of a fine brush, as described, for example, in patent FR 2 722 380. The applicator may be in the form of a block of foam or elastomer, a felt or a spatula. The applicator may be free (tuft or sponge) or of one piece with a rod carried by the closing element, as described, for example, in U.S. Pat. No. 5,492,426. The applicator may be of one piece with the container, as described, for example, by patent FR 2 761 959.

The product may be accommodated directly in the container, or indirectly. By way of example, the product may be arranged on an impregnated support, particularly in the form of a wipe or pad, and arranged (in unitary or plural form) in a box or in a sachet. A support of this kind, incorporating the product, is described for example in patent application WO 01/03538.

The closing element may be coupled to the container by screwing. Alternatively the coupling between the closing element and the container is performed other than by screwing, in particular via a bayonet mechanism, by snap-fastening, gripping, welding, adhesive bonding, or by magnetic attraction. By "snap-fastening" is meant, in particular, any system involving the traversal of a bead or cord of material by elastic deformation of a portion, particularly of the closing element, followed by return to the elastically unstressed position of the said portion after the traversal of the bead or cord.

The container may be at least partly made of thermoplastic material. Examples that may be mentioned of thermoplastic materials include polypropylene and polyethylene.

Alternatively the container is made of a non-thermoplastic material, particularly of glass or of metal (or alloy).

The container may be one with rigid walls or may have deformable walls, particularly in the form of a tube or tubular bottle.

The container may include means intended for distributing, or facilitating the distribution of, the composition. By way of example, the container may have walls which are deformable so as to allow the composition to exit in response to a positive pressure inside the container, this positive pressure being brought about by elastic (or non-elastic) squeezing of the container's walls. Alternatively, and particularly when the product is in the form of a stick, the product may be driven by a piston mechanism. Still in the case of a stick, particularly a makeup product stick (lipstick, foundation, etc.), the container may include a mechanism, especially a rack mechanism, or one with a threaded rod, or with a helical groove, which is capable of displacing a stick in the direction of the said opening. A mechanism of this kind is described for example in patent FR 2 806 273 or in patent FR 2 775 566. A mechanism of this kind for a liquid product is described in patent FR 2 727 609.

The container may be composed of a carton with a base delimiting at least one housing accommodating the composition, and a lid, particularly a lid articulated on the base, which is capable of covering the said base, at least in part. A carton of this kind is described for example in patent application WO 03/018423 or in patent FR 2 791 042.

The container may be equipped with a drainer arranged in the region of the opening of the container. A drainer of this kind allows the applicator to be wiped and optionally allows the rod, which may be of one piece with it, to be wiped. A drainer of this kind is described for example in patent FR 2 792 618.

The composition may be at the atmospheric pressure inside the container (at ambient temperature) or may be in pressurized form, particularly by means of a propellent gas (aerosol). In the latter case the container is equipped with a valve (of the type used for aerosols).

The content of the patents or patent applications cited above is incorporated by reference into the present application.

The examples which follow illustrate, without limitation, the compositions according to the invention.

EXAMPLE 4

Liquid Lipstick

| INGREDIENTS | % BY MASS |
| --- | --- |
| Polymer from Example 2 | 50.0 |
| Silica (Aerosil R 972 ®, Degussa) | 5.0 |
| Isododecane gelled with an ethylene/propylene/styrene copolymer and a butylene/ethylene/styrene copolymer (Versagel ® MD 970, Penreco) | 7.0 |
| Hydrogenated polyisobutene | 2.1 |
| Octyldodecanol | 0.9 |
| Phenyltrimethicone (DC 556, 20 cSt, Dow Corning) | 2.1 |
| Isododecane | 28.3 |
| Vinylpyrrolidone/1-eicosene copolymer (Antaron V-220 ®, ISP) | 1.2 |
| Pigments | 3.0 |
| Perfume | qs |

It can also be applied without difficulty using a foam applicator, and leads to a homogeneous deposit with good staying power.

EXAMPLE 5

Sun Composition

| Ingredients | (% by weight) |
|---|---|
| Glycerol | 6 |
| Propylene glycol | 6 |

-continued

| Ingredients | (% by weight) |
|---|---|
| Acrylates/$C_{10}$-$C_{30}$ alkyl acrylate copolymer PEMULEN TR-2 (Noveon) | 0.3 |
| Ammonium polyacryloyldimethyltaurate polymer (HOSTACERIN AMPS - Clariant) | 0.3 |
| Cyclohexasiloxane (DOW CORNING 246 FLUID - Dow Corning) | 6 |
| Xanthan gum RHODICARE XC (Rhodia) | 0.1 |
| Terephthalylidene dicamphor sulphonic acid (MEXORYL SX - Chimex) | 1.5 |
| Triethanolamine | qs |
| Octocrylene (UVINUL N539 - BASF) | 10 |
| Butylmethoxydibenzoylmethane (Parsol 1789 - Roche Vitamines) | 2.5 |
| Drometrizole trisiloxane (MEXORYL XL - Chimex) | 1.5 |
| $C_{12}$-$C_{15}$ alkyl benzoate (FINSOLV TN - Witco) | 4 |
| Polymer from Example 1 | 1 |
| Triethanolamine | 0.35 |
| Preservative and sequestrant | qs |
| Water | qs 100 |

EXAMPLES 6 to 11

Emulsion Mascaras

The following mascara compositions were prepared according to the invention and the prior art:

The prior art composition of Example 6 contains neither block polymer nor aqueous dispersion of particles of film-forming polymer.

The composition of Example 10 includes an aqueous dispersion of particles of film-forming polymer, but no block polymer.

The compositions of Examples 7 to 9 and 11, according to the invention, include a block polymer and an aqueous dispersion of particles of film-forming polymer.

| | Example 6 (comparative) | Example 7 (inventive) | Example 8 (inventive) | Example 9 (inventive) | Example 10 (comparative) | Example 11 (inventive) |
|---|---|---|---|---|---|---|
| Candelilla wax | 20 | 5 | 5 | 5 | 5 | |
| Aqueous polyurethane dispersion containing 38% AS ("Avalure UR-450 ®" from the company Goodrich) | | 8.3 (AS*) | | | | |
| Ethyl acrylate/methyl methacrylate (80/20) copolymer in aqueous dispersion containing 50% AS ("Daltosol 5000 AD ®" from DAITO) | | | 10 (AS) | | | |
| Acrylic and styrene/acrylic copolymer in aqueous dispersion containing 40% AS ("Syntran 5760" from the company Interpolymer) | | | | 8.7 (AS) | 17.42 (AS) | 6.37 (AS) |
| Block polymer from Example 3 | | 10 (AS) | 10 (AS) | 10 (AS) | | 15 (AS) |
| Stearic acid | | | | 5.8 | | |
| Triethanolamine stearate | | | | 2.9 | | |
| Black iron oxide | | | | 8 | | |
| Hydroxyethylcellulose | | | | 0.9 | | |
| Gum arabic | | | | 3.4 | | |
| Water, preservatives | | | | qs 100 | | |

*AS: active substance

For each composition, the dry extract, the load in vitro and the staying power are measured, according to the methods described below.

The load in vitro is measured by gravimetry on specimens of curled Caucasian hair (30 hairs, 1 cm long, distributed over a distance of 1 cm).

The specimen is made up by carrying out 3×10 passages of mascara spaced apart by 2 minutes, with collection of product between each series of 10.

The specimen is dried at ambient temperature for 10 minutes and then weighed.

This measurement is carried out on 6 specimens.

The load is the amount of material deposited on the specimen=mass of made-up specimen−mass of bare specimen.

The average load is the mean of the measurements carried out on the 6 specimens.

The solids content, in other words the amount of non-volatile material, or dry extract of the compositions is measured on a Mettler Toledo HG 53 balance (Halogen Moisture Analyzer). A sample of mascara (2-3 g) is placed on an aluminium boat and subjected to a temperature of 120° C. for 60 minutes. The dry extract measurement corresponds to the monitoring of the mass of the sample over time. The final solids content is therefore the percentage of the final mass (after 60 minutes) relative to the initial mass: SC=(final mass/initial mass)×100.

The staying power of the film formed by the composition according to the invention is evaluated by measuring the water resistance, over time, of a film of composition spread onto a glass plate and subjected to stirring in aqueous medium. The protocol is as follows:

At ambient temperature (25° C.) a layer of composition 300 μm thick (before drying) with a surface area of 9 cm×9 cm is spread over a glass plate with a surface area of 10 cm×10 cm, and then left to dry at 30° C. and 50% relative humidity for 24 hours. After drying, the plate is placed in a 2-liter crystallizer with a diameter of 19 cm, which is filled with one liter of water and placed on a heating magnetic stirrer sold under the name RCT basic by the company IKA labortechnik. A smooth cylindrical magnetic PTFE bar (length 6 cm; diameter 1 cm) is then placed on the film. The stirring speed is set to position 5. The water temperature is regulated by means of a thermometer to a temperature of 20° C. or 40° C. At time $t_0=0$, stirring is commenced. A measurement is made of the time t (expressed in minutes) after which the film begins to detach or disbond from the plate or when a hole the size of the magnetic stirring bar is observed, in other words when the hole has a diameter of 6 cm.

The water resistance of the film corresponds to the measured time t.

The results obtained are as follows:

|  | Example 6 (comparative) | Example 7 (inventive) | Example 8 (inventive) | Example 9 (inventive) | Example 10 (comparative) | Example 11 (inventive) |
|---|---|---|---|---|---|---|
| Measured solids content (%) | 38.8 | 43.8 | 45.2 | 44.9 | 41.6 | 41.8 |
| Load in vitro (mg) |  | 11.90 ± 1.34 | 12.5 ± 1.42 | 10.18 ± 1.54 | 7.43 ± 0.65 | 11.17 ± 0.74 |
| Staying power | 55" | 1'24" | 2'24" | 6'26" | 38' | 19' |

It is found that the compositions according to the invention, of Examples 7 to 9 and 11, comprising the combination of an aqueous dispersion of particles of film-forming polymer and a block polymer, exhibit a good staying power, better than that of the composition of Example 10 which does not contain block polymer. Moreover, the compositions according to the invention allow the lashes to be made up thickly, since they have a high solids content and high levels of load in vitro.

EXAMPLE 12

Waterproof Mascara

The following mascara, according to the invention, was prepared:

| Carnauba wax | 4.7 |
|---|---|
| Beeswax | 8.2 |
| Rice bran wax | 2.2 |
| Modified hectorite ("Bentone 38V ®" from Elementis) | 5.5 |
| Paraffin wax | 2.2 |
| Talc | 1 |
| Vinyl acetate/allyl stearate copolymer (Mexomere PQ from the company Chimex) | 6.7 |
| Block polymer from Example 1 | 10 |
| Polyvinyl laurate (Mexomere PP from the company Chimex) | 0.7 |
| Sulphopolyester (Eastman AQ 55S from Eastman) | 0.1 |
| Preservatives | 0.2 |
| Propylene carbonate | 1.8 |
| Water | 7 |

-continued

| Pigments | 5.2 |
|---|---|
| Isododecane | qs 100 |

Measurements were made of the solids content, the load in vitro and the staying power, according to the measurement methods described above in the description.

The following results were obtained:

| Measured solids content (%) | 45.4 |
|---|---|
| Load in vitro (mg) | 8.9 ± 0.9 |
| Staying power | Greater than one day (24 h) |

This mascara exhibits good staying power while having a good thickening (loading) effect on the lashes.

The invention claimed is:

1. A cosmetic composition comprising an organic liquid medium, at least one film-forming ethylenic linear block polymer free from styrene units, and at least one other film former which is soluble or dispersible in the organic liquid medium, wherein the at least one film-forming ethylenic linear block polymer has a polydispersity index ranging from 2.5 to 8 and comprises a first block and a second block of different glass transition temperatures (Tg), wherein the first and second blocks are linked together via an intermediate segment that is different from the first and second blocks and comprises at least one constituent monomer of the first block and at least one constituent monomer of the second block, wherein the at least one constituent monomer of the first block differs from the at least one constituent monomer of the second block, the intermediate segment is a random copolymer block, and the first block of the polymer is a block with a Tg of greater than or equal to 40° C., and the second block is a block with a Tg of less than or equal to 20° C., wherein the first block is derived from at least one monomer chosen from:

methacrylates of formula $CH_2=C(CH_3)-COOR_1$ wherein $R_1$ is chosen from linear and branched unsubstituted alkyl groups comprising from 1 to 4 carbon atoms, and from $C_4$ to $C_{12}$ cycloalkyl groups;

acrylates of formula $CH_2=CH-COOR_2$ wherein $R_2$ is chosen from $C_4$ to $C_{12}$ cycloalkyl groups; and (meth)acrylamides of formula:

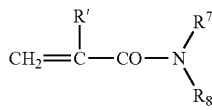

where $R_7$ and $R_8$, which are identical or different, are chosen from hydrogen atoms and from linear and branched alkyl groups comprising 1 to 12 carbon atoms; or alternatively $R_7$ is a H atom and $R_8$ is a 1,1-dimethyl-3-oxobutyl group and R' is chosen from H and methyl, wherein the second block is derived from at least one monomer chosen from:

acrylates of formula $CH_2=CHCOOR_3$, wherein $R_3$ is chosen from linear and branched $C_1$ to $C_{12}$ unsubstituted alkyl groups, with the proviso that the alkyl groups are not chosen from a tert-butyl group;

methacrylates of formula $CH_2=C(CH_3)-COOR_4$, wherein $R_4$ is chosen from linear and branched $C_6$ to $C_{12}$ unsubstituted alkyl groups;

vinyl esters of formula $R_5-CO-O-CH=CH_2$ wherein $R_5$ is chosen from linear and branched $C_4$ to $C_{12}$ alkyl groups;

$C_4$ to $C_{12}$ alkyl vinyl ethers; and

N—($C_4$ to $C_{12}$ alkyl)acrylamides, wherein the intermediate block does not comprise acrylates or methacrylates comprising a COOR side chain in which R comprises an intercalated heteroatom chosen from O, N and S, wherein the first and the second blocks are incompatible in the organic liquid medium, and wherein the at least one film-forming ethylenic linear block polymer is non-elastomeric.

2. A cosmetic composition comprising an organic liquid medium, at least one aqueous phase, at least one film-forming ethylenic linear block polymer free from styrene units, and at least one other film former which is soluble or dispersible in the aqueous phase, wherein the at least one film-forming ethylenic linear block polymer has a polydispersity index ranging from 2.5 to 8 and comprises a first block and a second block of different glass transition temperatures (Tg), wherein the first and second blocks are linked together via an intermediate segment that is different from the first and second blocks and comprises at least one constituent monomer of the first block and at least one constituent monomer of the second block, wherein the at least one constituent monomer of the first block differs from the at least one constituent monomer of the second block, the intermediate segment is a random copolymer block, and the first block of the polymer is a block with a Tg of greater than or equal to 40° C., and the second block is a block with a Tg of less than or equal to 20° C., wherein the first block is derived from at least one monomer chosen from:

methacrylates of formula $CH_2=C(CH_3)-COOR_1$ wherein $R_1$ is chosen from linear and branched unsubstituted alkyl groups comprising from 1 to 4 carbon atoms, and from $C_4$ to $C_{12}$ cycloalkyl groups;

acrylates of formula $CH_2=CH-COOR_2$ wherein $R_2$ is chosen from $C_4$ to $C_{12}$ cycloalkyl groups; and (meth)acrylamides of formula:

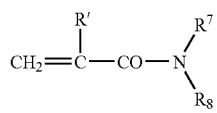

where $R_7$ and $R_8$, which are identical or different, are chosen from hydrogen atoms and from linear and branched alkyl groups comprising 1 to 12 carbon atoms; or alternatively $R_7$ is a H atom and $R_8$ is a 1,1-dimethyl-3-oxobutyl group and R' is chosen from H and methyl, wherein the second block is derived from at least one monomer chosen from:

acrylates of formula $CH_2=CHCOOR_3$, wherein $R_3$ is chosen from linear and branched $C_1$ to $C_{12}$ unsubstituted alkyl groups, with the proviso that the alkyl groups are not chosen from a tert-butyl group;

methacrylates of formula $CH_2=C(CH_3)-COOR_4$, wherein $R_4$ is chosen from linear and branched $C_6$ to $C_{12}$ unsubstituted alkyl groups;

vinyl esters of formula $R_5-CO-O-CH=CH_2$ wherein $R_5$ is chosen from linear and branched $C_4$ to $C_{12}$ alkyl groups;

$C_4$ to $C_{12}$ alkyl vinyl ethers; and

N—($C_4$ to $C_{12}$ alkyl)acrylamides, wherein the intermediate block does not comprise acrylates or methacrylates comprising a COOR side chain in which R comprises an intercalated heteroatom chosen from O, N and S, wherein the first and the second blocks are incompatible in the organic liquid medium, and wherein the at least one film-forming ethylenic linear block polymer is non-elastomeric.

3. The cosmetic composition according to claim 1, wherein the at least one film-forming ethylenic linear block polymer is an ethylenic polymer obtained from aliphatic ethylenic monomers comprising a carbon-carbon double bond and at least one ester group —COO— or amide group —CON—.

4. The cosmetic composition according to claim 1, wherein the at least one film-forming ethylenic linear block polymer is not soluble at an amount of active substance of at least 1% by weight in water or in a mixture of water and linear or branched lower monoalcohols comprising 2 to 5 carbon atoms, without a change in pH, at ambient temperature (25° C.).

5. The cosmetic composition according to claim 1, wherein the intermediate segment has a glass transition temperature between the glass transition temperatures of the first and the second blocks.

6. The cosmetic composition according to claim 1, wherein the first block comprises at least one monomer chosen from methyl methacrylate, isobutyl (meth)acrylate, and isobornyl (meth)acrylate.

7. The cosmetic composition according to claim 1, wherein the second block comprises at least one monomer chosen from alkyl acrylates wherein the alkyl chain comprises from 1 to 10 carbon atoms, with the exception of the tert-butyl group.

8. The cosmetic composition according to claim 1, wherein the first block is a copolymer.

9. The cosmetic composition according to claim 1, wherein the first block is present in an amount ranging from 20% to 90% by weight, relative to the total weight of the polymer.

10. The cosmetic composition according to claim 9, wherein the first block is present in an amount ranging from 50% to 70% by weight, relative to the total weight of the polymer.

11. The cosmetic composition according to claim 1, wherein the second block is a homopolymer.

12. The cosmetic composition according to claim 1, wherein the second block is present in an amount ranging from 5% to 75% by weight relative to the total weight of the polymer.

13. The cosmetic composition according to claim 12, wherein the second block is present in an amount ranging from 25% to 45% by weight relative to the total weight of the polymer.

14. The cosmetic composition according to claim 1, wherein at least one of the first block and the second block comprises at least one additional monomer chosen from:
- ethylenically unsaturated monomers comprising at least one carboxylic or sulphonic acid function;
- ethylenically unsaturated monomers comprising at least one tertiary amine function;
- methacrylates of formula $CH_2=C(CH_3)-COOR_6$ wherein $R_6$ is chosen from linear and branched alkyl groups comprising from 1 to 4 carbon atoms, the alkyl group being substituted by at least one substituent chosen from hydroxyl groups and halogen atoms chosen from Cl, Br, I and F;
- methacrylates of formula $CH_2=C(CH_3)-COOR_9$, wherein $R_9$ is chosen from linear and branched $C_6$ to $C_{12}$ alkyl groups, the alkyl group being substituted by at least one substituent chosen from halogen atoms chosen from Cl, Br, I and F; and
- acrylates of formula $CH_2=CHCOOR_{10}$, wherein $R_{10}$ is chosen from linear and branched $C_1$ to $C_{12}$ alkyl groups substituted by at least one substituent chosen from hydroxyl groups and halogen atoms chosen from Cl, Br, I and F, or $R_{10}$ is a $C_1$ to $C_{12}$ alkyl-O-POE (polyoxyethylene) with repetition of the oxyethylene unit from 5 to 30 times, or $R_{10}$ is a polyoxyethylenated group comprising from 5 to 30 ethylene oxide units and
wherein the ethylenically unsaturated monomers comprising at least one silicon atom are chosen from methacryloxypropyltrimethoxysilane and methacryloxy-propyl-tris(trimethylsiloxy)silane.

15. The cosmetic composition according to claim 14, wherein each of the first and the second blocks comprises at least one additional monomer chosen from acrylic acid, (meth)acrylic acid, and trifluoroethyl methacrylate.

16. The cosmetic composition according to claim 14, wherein each of the first and the second blocks comprises at least one monomer chosen from esters of (meth)acrylic acid and optionally the at least one additional monomer.

17. The cosmetic composition according to claim 14, wherein the at least one additional monomer is present in an amount ranging from 1% to 30% by weight of the total weight of the first and/or the second blocks.

18. The cosmetic composition according to claim 1, wherein the difference between the glass transition temperatures (Tg) of the first and the second blocks is greater than 40° C.

19. The cosmetic composition according to claim 1, wherein the at least one film-forming ethylenic linear block polymer has a weight-average mass (Mw) of less than or equal to 300 000.

20. The cosmetic composition according to claim 19, wherein the weight-average mass (Mw) ranges from 35 000 to 200 000.

21. The cosmetic composition according to claim 19, wherein the weight-average mass (Mw) ranges from 45 000 to 150 000.

22. The cosmetic composition according to claim 19, wherein the weight-average mass (Mw) is less than or equal to 70 000.

23. The cosmetic composition according to claim 22, wherein the weight-average mass (Mw) ranges from 10 000 to 60 000.

24. The cosmetic composition according to claim 23, wherein the weight-average mass (Mw) ranges from 12 000 to 50 000.

25. The cosmetic composition according to claim 1, wherein the composition comprises from 0.1% to 60% by weight of polymer active substance.

26. The cosmetic composition according to claim 25, wherein the composition comprises from 10% to 40% by weight of polymer active substance.

27. The cosmetic composition according to claim 1, wherein the at least one other film former is a film-forming polymer which is soluble in the organic liquid medium.

28. The cosmetic composition according to claim 27, wherein the at least one other film former is a fat-soluble film-forming polymer.

29. The cosmetic composition according to claim 28, wherein the fat-soluble film-forming polymer is chosen from the fat-soluble, amorphous homopolymers and copolymers of olefins, of cycloolefins, of butadiene, of isoprene, of styrene, of vinyl ethers, esters or of amides, and of (meth)acrylic acid esters and amides comprising a linear, branched or cyclic $C_{4-50}$ alkyl group.

30. The cosmetic composition according to claim 28, wherein the fat-soluble film-forming polymer is chosen from homopolymers and copolymers comprising monomers chosen from isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate, stearyl (meth)acrylate, and mixtures thereof.

31. The cosmetic composition according to claim 28, wherein the fat-soluble film-forming polymer is chosen from amorphous and fat-soluble polycondensates.

32. The cosmetic composition according to claim 28, wherein the fat-soluble film-forming polymer is chosen from amorphous and fat-soluble polysaccharides comprising alkyl (ether or ester) side chains.

33. The cosmetic composition according to claim 28, wherein the fat-soluble film-forming polymer bears fluoro groups.

34. The cosmetic composition according to claim 33, wherein the fat-soluble film-forming polymer bearing fluoro groups is chosen from alkyl (meth)acrylate/perfluoroalkyl (meth)acrylate copolymers.

35. The cosmetic composition according to claim 28, wherein the fat-soluble film-forming polymer is chosen from polymers and copolymers resulting from the polymerization or copolymerization of an ethylenic monomer comprising at least one ethylenic bond.

36. The cosmetic composition according to claim 35, wherein the polymer and copolymer resulting from the polymerization or copolymerization of an ethylenic monomer are chosen from polystyrene/copoly(ethylene/butylene)s.

37. The cosmetic composition according to claim 28, wherein the fat-soluble film-forming polymer is chosen from polymers comprising a non-silicone organic skeleton grafted with monomers comprising a polysiloxane.

38. The cosmetic composition according to claim 28, wherein the fat-soluble film-forming polymer is chosen from silicone polymers grafted with non-silicone organic monomers.

39. The cosmetic composition according to claim 1, wherein the at least one other film former is a film-forming polymer which is dispersible in the organic liquid medium.

40. The cosmetic composition according to claim 39, wherein the organic liquid medium comprises at least one oil, in which the film former is dispersible, and wherein the film former is in the form of a non-aqueous dispersion of polymer particles.

41. The cosmetic composition according to claim 2, wherein the at least one other film former is a film-forming polymer which is dispersible in the aqueous phase.

42. The cosmetic composition according to claim 41, wherein the film-forming polymer which is dispersible in the aqueous phase is chosen from polyurethanes, polyurethane-acrylics, polyurethane-polyvinylpyrrolidones, polyester-polyurethanes, polyether-polyurethanes, polyureas, polyurea/polyurethanes, and mixtures thereof.

43. The cosmetic composition according to claim 41, wherein the film-forming polymer which is dispersible in the aqueous phase is an aliphatic, cycloaliphatic or aromatic polyurethane copolymer, or a polyurea/polyurethane or polyurea copolymer comprising:
at least one block of linear or branched aliphatic and cycloaliphatic and/or aromatic polyester origin, and/or
at least one block of aliphatic and/or cycloaliphatic and/or aromatic polyether origin, and/or
at least one substituted or unsubstituted, branched or unbranched silicone block and/or
at least one block comprising fluoro groups.

44. The cosmetic composition according to claim 41, wherein the film-forming polymer which is dispersible in the aqueous phase is chosen from polyesters, polyesteramides, fatty-chain polyesters, polyamides and epoxy ester resins.

45. The cosmetic composition according to claim 41, wherein the film-forming polymer which is dispersible in the aqueous phase is chosen from acrylic polymers, acrylic copolymers and vinyl polymers.

46. The cosmetic composition according to claim 1, wherein the at least one other film former is present in an amount ranging from 2% to 60% by weight of dry compound relative to the total weight of the composition.

47. The cosmetic composition according to claim 1, wherein the at least one other film former is present in an amount ranging from 2% to 30% by weight of dry compound relative to the total weight of the composition.

48. The cosmetic composition according to claim 1, further comprising at least one colorant chosen from water-soluble dyes and pulverulent colorants.

49. The cosmetic composition according to claim 1, wherein the composition is in a form chosen from a suspension, dispersion, solution, gel, emulsion cream, paste, mousse, a vesicle dispersion, a two-phase lotion, a multi-phase lotion, a spray, powder, paste, a stick and a cast solid.

50. The cosmetic composition according to claim 1, wherein the composition is in anhydrous form.

51. The cosmetic composition according to claim 1, wherein the composition is in a form chosen from a composition for making up or caring for keratin materials, a lip makeup product, an eye makeup product, a complexion makeup product, a nail makeup product.

52. A composition for coating keratin fibers, comprising an organic liquid medium, at least one aqueous phase, at least one film-forming ethylenic linear block polymer and at least one other film former soluble or dispersible in the aqueous phase,
wherein the at least one film-forming ethylenic linear block polymer has a polydispersity index ranging from 2.5 to 8 and comprises a first block and a second block of different glass transition temperatures (Tg),
wherein the first and second blocks are linked together via an intermediate segment that is different from the first and second blocks and comprises at least one constituent monomer of the first block and at least one constituent monomer of the second block,
wherein the at least one constituent monomer of the first block differs from the at least one constituent monomer of the second block, the intermediate segment is a random copolymer block, and the first block of the polymer is a block with a Tg of greater than or equal to 40° C., and the second block is a block with a Tg of less than or equal to 20° C.,
wherein the first block is derived from at least one monomer chosen from:
methacrylates of formula $CH_2=C(CH_3)-COOR_1$
wherein $R_1$ is chosen from linear and branched unsubstituted alkyl groups comprising from 1 to 4 carbon atoms, and from $C_4$ to $C_{12}$ cycloalkyl groups;
acrylates of formula $CH_2=CH-COOR_2$
wherein $R_2$ is chosen from $C_4$ to $C_{12}$ cycloalkyl groups; and
(meth)acrylamides of formula:
wherein the at least one film-forming ethylenic linear block polymer is non-elastomeric.

53. The composition according to claim 52, wherein the at least one other film former is a film-forming polymer dispersible in the aqueous phase.

54. The composition according to claim 53, wherein said at least one other film-forming polymer dispersible in the aqueous phase is chosen from polyurethanes, polyurethane-acrylics, polyurethane-polyvinylpyrrolidones, polyester-polyurethanes, polyether-polyurethanes, polyureas, polyurea/polyurethanes, and mixtures thereof.

55. The composition according to claim 52, further comprising at least one wax.

56. The composition according to claim 52, further comprising at least one surfactant.

57. The composition according to claim 52, further comprising at least one second film former chosen from water-soluble polymers.

58. The composition according to claim 57, wherein the water-soluble polymers are chosen from cationic cellulose derivatives and/or optionally modified polymers of natural origin.

59. The composition according to claim 52, further comprising a colorant.

60. The composition according to claim 52, wherein the composition is in the form of a mascara.

61. A cosmetic kit comprising:
a) a container delimiting at least one compartment, the container being closed by a closing element; and
b) a composition disposed inside the compartment, the composition comprising an organic liquid medium, at least one film-forming ethylenic linear block polymer free from styrene units, and at least one other film former which is soluble or dispersible in the organic liquid medium,
wherein the at least one film-forming ethylenic linear block polymer has a polydispersity index ranging from 2.5 to 8 and comprises a first block and a second block of different glass transition temperatures (Tg),
wherein the first and second blocks are linked together via an intermediate segment that is different from the first and second blocks and comprises at least one constituent monomer of the first block and at least one constituent monomer of the second block,
wherein the at least one constituent monomer of the first block differs from the at least one constituent monomer of the second block, the intermediate segment is a random copolymer block, and the first block of the polymer is a block with a Tg of greater than or equal to 40° C., and the second block is a block with a Tg of less than or equal to 20° C., wherein the first block is derived from at least one monomer chosen from:
  methacrylates of formula $CH_2=C(CH_3)-COOR_1$
wherein $R_1$ is chosen from linear and branched unsubstituted alkyl groups comprising from 1 to 4 carbon atoms, and from $C_4$ to $C_{12}$ cycloalkyl groups;
  acrylates of formula $CH_2=CH-COOR_2$
wherein $R_2$ is chosen from $C_4$ to $C_{12}$ cycloalkyl groups; and
  (meth)acrylamides of formula:

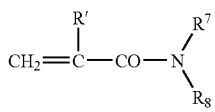

where $R_7$ and $R_8$, which are identical or different, are chosen from hydrogen atoms and from linear and branched alkyl groups comprising 1 to 12 carbon atoms; or alternatively $R_7$ is a H atom and $R_8$ is a 1,1-dimethyl-3-oxobutyl group and R' is chosen from H and methyl,
wherein the second block is derived from at least one monomer chosen from:
  acrylates of formula $CH_2=CHCOOR_3$,
wherein $R_3$ is chosen from linear and branched $C_1$ to $C_{12}$ unsubstituted alkyl groups, with the proviso that the alkyl groups are not chosen from a tert-butyl group;
  methacrylates of formula $CH_2=C(CH_3)-COOR_4$,
wherein $R_4$ is chosen from linear and branched $C_6$ to $C_{12}$ unsubstituted alkyl groups;
  vinyl esters of formula $R_5-CO-O-CH=CH_2$
wherein $R_5$ is chosen from linear and branched $C_4$ to $C_{12}$ alkyl groups;
  $C_4$ to $C_{12}$ alkyl vinyl ethers; and
  $N-(C_4$ to $C_{12}$ alkyl)acrylamides,
wherein the intermediate block does not comprise acrylates or methacrylates comprising a COOR side chain in which R comprises an intercalated heteroatom chosen from O, N and S,
wherein the first and the second blocks are incompatible in the organic liquid medium, and
wherein the at least one film-forming ethylenic linear block polymer is non-elastomeric.

62. The cosmetic kit according to claim 61, wherein the container is formed, at least partly, of at least one thermoplastic material.

63. The cosmetic kit according to claim 61, wherein the container is formed, at least partly, of at least one non-thermoplastic material.

64. The cosmetic kit according to claim 61, wherein in the closed position of the container, the closing element is screwed onto the container.

65. The cosmetic kit according to claim 61, wherein in the closed position of the container, the closing element is coupled to the container other than by screwing.

66. The cosmetic kit according to claim 61, wherein the composition is substantially at atmospheric pressure inside the compartment.

67. The cosmetic kit according to claim 61, wherein the composition is pressurized inside the container.

68. A method of making up or caring for keratin materials, comprising the application to the keratin materials of a cosmetic composition comprising an organic liquid medium, at least one film-forming ethylenic linear block polymer free from styrene units, and at least one other film former which is soluble or dispersible in the organic liquid medium,
wherein the at least one film-forming ethylenic linear block polymer has a polydispersity index ranging from 2.5 to 8 and comprises a first block and a second block of different glass transition temperatures (Tg),
wherein the first and second blocks are linked together via an intermediate segment that is different from the first and second blocks and comprises at least one constituent monomer of the first block and at least one constituent monomer of the second block,
wherein the at least one constituent monomer of the first block differs from the at least one constituent monomer of the second block, the intermediate segment is a random copolymer block, and the first block of the polymer is a block with a Tg of greater than or equal to 40° C., and the second block is a block with a Tg of less than or equal to 20° C.,
wherein the first block is derived from at least one monomer chosen from:
  methacrylates of formula $CH_2=C(CH_3)-COOR_1$
wherein $R_1$ is chosen from linear and branched unsubstituted alkyl groups comprising from 1 to 4 carbon atoms, and from $C_4$ to $C_{12}$ cycloalkyl groups;
  acrylates of formula $CH_2=CH-COOR_2$
wherein $R_2$ is chosen from $C_4$ to $C_{12}$ cycloalkyl groups; and
  (meth)acrylamides of formula:

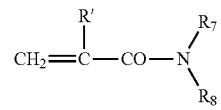

where $R_7$ and $R_8$, which are identical or different, are chosen from hydrogen atoms and from linear and branched alkyl groups comprising 1 to 12 carbon atoms; or

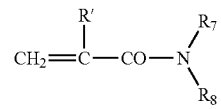

where $R_7$ and $R_8$, which are identical or different, are chosen from hydrogen atoms and from linear and branched alkyl groups comprising 1 to 12 carbon atoms; or alternatively $R_7$ is a H atom and $R_8$ is a 1,1-dimethyl-3-oxobutyl group and R' is chosen from H and methyl,
wherein the second block is derived from at least one monomer chosen from:
  acrylates of formula $CH_2=CHCOOR_3$,
wherein $R_3$ is chosen from linear and branched $C_1$ to $C_{12}$ unsubstituted alkyl groups, with the proviso that the alkyl groups are not chosen from a tert-butyl group;
  methacrylates of formula $CH_2=C(CH_3)-COOR_4$,
wherein $R_4$ is chosen from linear and branched $C_6$ to $C_{12}$ unsubstituted alkyl groups;
  vinyl esters of formula $R_5-CO-O-CH=CH_2$
wherein $R_5$ is chosen from linear and branched $C_4$ to $C_{12}$ alkyl groups;
  $C_4$ to $C_{12}$ alkyl vinyl ethers; and
  $N-(C_4$ to $C_{12}$ alkyl)acrylamides,
wherein the intermediate block does not comprise acrylates or methacrylates comprising a COOR side chain in which R comprises an intercalated heteroatom chosen from O, N and S, wherein the first and the second blocks are incompatible in the organic liquid medium, and
alternatively $R_7$ is a H atom and $R_8$ is a 1,1-dimethyl-3-oxobutyl group and R' is chosen from H and methyl,
  wherein the second block is derived from at least one monomer chosen from:
    acrylates of formula $CH_2$=$CHCOOR_3$,
  wherein $R_3$ is chosen from linear and branched $C_1$ to $C_{12}$ unsubstituted alkyl groups, with the proviso that the alkyl groups are not chosen from a tert-butyl group;
    methacrylates of formula $CH_2$=$C(CH_3)$—$COOR_4$,
  wherein $R_4$ is chosen from linear and branched $C_6$ to $C_{12}$ unsubstituted alkyl groups;
    vinyl esters of formula $R_5$—CO—O—CH=$CH_2$
  wherein $R_5$ is chosen from linear and branched $C_4$ to $C_{12}$ alkyl groups;
    $C_4$ to $C_{12}$ alkyl vinyl ethers; and
    N—($C_4$ to $C_{12}$ alkyl)acrylamides,
  wherein the intermediate block does not comprise acrylates or methacrylates comprising a COOR side chain in which R comprises an intercalated heteroatom chosen from O, N and S,
  wherein the first and the second blocks are incompatible in the organic liquid medium, and
  wherein the at least one film-forming ethylenic linear block polymer is non-elastomeric.

* * * * *